United States Patent [19]

Ebetino et al.

[11] Patent Number: 5,731,299
[45] Date of Patent: Mar. 24, 1998

[54] PHOSPHONOSULFONATE COMPOUNDS, PHARMACEUTICAL COMPOSITIONS, AND METHODS FOR TREATING ABNORMAL CALCIUM AND PHOSPHATE METABOLISM

[75] Inventors: Frank Hallock Ebetino; Allan Vincent Bayless, both of Cincinnati, Ohio; Susan Mary Dansereau, Sherburne, N.Y.

[73] Assignee: The Procter & Gamble Company, Cincinnati, Ohio

[21] Appl. No.: 55,809

[22] Filed: May 7, 1993

Related U.S. Application Data

[63] Continuation-in-part of Ser. No. 890,885, May 29, 1992, abandoned, and a continuation-in-part of Ser. No. 891,487, May 29, 1992, abandoned, and a continuation-in-part of Ser. No. 891,355, May 29, 1992, abandoned, and a continuation-in-part of Ser. No. 891,490, May 29, 1992, abandoned, and a continuation-in-part of Ser. No. 890,886, May 29, 1992, abandoned, and a continuation-in-part of Ser. No. 891,309, May 29, 1992, abandoned.

[51] Int. Cl.[6] ............... C07F 13/00; C07F 15/02; C07F 9/38; C07F 9/40; C07F 9/58; C07D 213/69; C07C 143/68; A61K 49/00

[52] U.S. Cl. ............... 514/79; 558/45; 514/80; 514/81; 514/86; 514/89; 514/92; 514/94; 514/114; 514/127; 544/232; 544/243; 544/244; 540/471; 540/450; 540/474; 540/542; 546/22; 546/23; 548/112; 548/113; 562/11; 562/17; 562/23; 562/24

[58] Field of Search ............... 558/45; 562/11, 562/17, 24, 23, 35; 546/22, 23; 548/112, 113; 544/232, 243, 244; 540/450, 474, 471, 542; 514/79, 80, 81, 88, 89, 92, 94, 114, 127

[56] References Cited

U.S. PATENT DOCUMENTS

| | | | |
|---|---|---|---|
| 2,336,230 | 12/1943 | Dickey et al. | 558/45 X |
| 3,819,676 | 6/1974 | Christensen et al. | 558/45 |
| 4,032,521 | 6/1977 | Christensen et al. | 260/243 |
| 4,059,431 | 11/1977 | Takematsu et al. | 558/45 X |
| 4,781,865 | 11/1988 | Liu | 558/45 X |
| 4,937,367 | 6/1990 | Castaldi et al. | 558/45 X |
| 4,959,360 | 9/1990 | Lafferty et al. | 514/217 |
| 5,011,938 | 4/1991 | Barnett et al. | 548/359 |
| 5,272,128 | 12/1993 | Rosen et al. | 558/45 X |

FOREIGN PATENT DOCUMENTS

| | | | |
|---|---|---|---|
| 0 477 454 A1 | 4/1992 | European Pat. Off. | C07H 19/10 |
| 0 508 687 A1 | 10/1992 | European Pat. Off. | C07H 19/20 |
| 0284986 | 10/1970 | U.S.S.R. | 558/45 |
| 0585172 | 12/1977 | U.S.S.R. | 558/45 |
| 0756099 | 8/1956 | United Kingdom | 588/45 |
| 2 248 831 | 4/1992 | United Kingdom | C02F 5/14 |
| 2 248 832 | 4/1992 | United Kingdom | C02F 5/14 |
| WO 90/07480 A | 7/1990 | WIPO | C07C 5/22 |
| WO/90-7513 | 7/1990 | WIPO | 558/45 |
| WO 91/12822 | 9/1991 | WIPO | A61K 40/00 |

OTHER PUBLICATIONS

B. Musicki et al., "Synthesis of Nucleoside and Sulfonates and Sulfones" Tetrahedron Letters, vol. 32, No. 10, pp. 1267–1270, 1991.

D.J. Burton et al., "Synthesis of (Sulfodifluoromethyl)phosphonic Acid", *J. American Chemical Society*, vol. 111, No. 5, pp. 1773–1776, 1989.

J.C. Carretero et al., "Synthesis of α,β–Unsaturated Sulphonates Via the Wittig–Horner Reaction", *Tetrahebron*, vol. 43, No. 21, pp. 5125–5134, 1987.

Primary Examiner—Floyd D. Higel
Attorney, Agent, or Firm—David L. Suter; Carl J. Roof; Richard A. Hake

[57] ABSTRACT

The present invention relates to phosphonsulfonates and the pharmaceutically-acceptable salts and esters thereof, having the following structure according to formula (I):

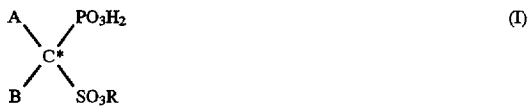

The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals, including treating or preventing osteoporosis and arthritis, especially rheumatoid arthritis and osteoarthritis. This method comprises administering to a human or other mammal in need of such treatment of a safe and effective amount of a compound or composition of the present invention.

33 Claims, No Drawings

PHOSPHONOSULFONATE COMPOUNDS, PHARMACEUTICAL COMPOSITIONS, AND METHODS FOR TREATING ABNORMAL CALCIUM AND PHOSPHATE METABOLISM

This is a continuation-in-part of U.S. patent application Ser. Nos. 07/890,885, (abandoned) 07/891,487, (abandoned) 07/891,355, (abandoned) 07/891,490, (abandoned) 07/890,886, (abandoned) and 07/891,309, (abandoned) all filed May 29, 1992.

BACKGROUND OF THE INVENTION

This invention relates to novel phosphonosulfonate compounds. This invention further relates to pharmaceutical compositions containing these novel compounds, as well as to methods for treating or preventing metabolic bone disorders characterized by abnormal calcium and phosphate metabolism by utilizing a compound or pharmaceutical composition of the present invention. Specifically, this invention relates to methods for treating or preventing osteoporosis, or arthritis, especially rheumatoid arthritis and osteoarthritis, by utilizing a compound or pharmaceutical composition of the present invention.

A number of pathological conditions which can afflict humans and warm blooded animals involve abnormal calcium and phosphate metabolism. Such conditions may be divided into two broad categories:

(1) Conditions which are characterized by anomalous mobilization of calcium and phosphate leading to general or specific bone loss, such as osteoporosis and Paget's disease, or excessively high calcium and phosphate levels in the fluids of the body, such as hypercalcemia of tumor origin. Such conditions are sometimes referred to herein as pathological hard tissue demineralizations.

(2) Conditions which cause or result from deposition of calcium and phosphate anomalously in the body, such as arthritis, including rheumatoid arthritis and osteoarthritis. These conditions are sometimes referred to herein as pathological calcifications.

The first category includes the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adrenocorticoid, as can occur in steroid therapy); disease-induced (arthritic and tumor), etc.; however, the manifestations are essentially the same.

In general, there are two types of osteoporosis: primary and secondary. "Secondary osteoporosis" is the result of a separate disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment consists primarily of calcium and estrogen administration.

In addition to osteoporosis, bone loss can result from arthritis, including rheumatoid arthritis and osteoarthritis. Rheumatoid arthritis is a chronic, systemic and particular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

Osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening and painful movement.

A variety of polyphosphonic acid derivatives have been proposed for use in the treatment and prophylaxis of diseases involving abnormal calcium and phosphate metabolism. For example, numerous references all incorporated by reference herein, disclose compositions containing polyphosphonates, in particular bisphosphonates, such as ethane-1-hydroxy-1,1diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe substituted phosphonic acids useful for the treatment of osteoporosis and/or arthritis, and are hereby incorporated by reference herein: U.S. Pat. No. 5,071,840 to Ebetino, et al, issued Dec. 10, 1991, U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; U.S.

Patent to Breliere, et al., issued May 24, 1988; U.S. Pat. No. 4,876,247 to Barbier, et al., issued Oct. 24, 1989; European Patent Application Publication No. 100,718, of Breliere S. A., published Feb. 15, 1984; European Patent Application Publication No. 170,228, of Boehfinger Mannheim GmbH, published Feb. 5, 1986; European Patent Application Publication No. 186,405, of Benedict and Perkins, published Jul. 2, 1986; European Patent Application Publication No. 298,553, of Ebetino, published Jan. 11, 1989; U.S. Pat. No. 4,754,993, to Bosies, et al., issued Nov. 15, 1988; U.S. Pat. No. 4,939,130 to Jaeggi, et al., issued Jul. 3, 1990; U.S. Pat. No. 4,971,958 to Bosies, et al., issued Nov. 20, 1990; WO 90/12017 to Dunn, et al., published Oct. 18, 1990; WO 91/10646 to Youssefyeh, R., et al., published Jul. 25, 1991; AU-A-26738/88 to Jaeggi, K. A., publication date Jun. 15, 1989; AU-A45467/89 of Ciba-Geigy, publication date May 31, 1990.

A limited number of phosphonosulfonate-containing compounds are disclosed in the literature. See for example, U.S. Pat. No. 4,032,521, to Christiansen et al., issued Jun. 28, 1977; PTC Patent Publication 90/07480, by King et al., published Jul. 12, 1990; Great Britain Patent Publication No. 2,248,831, by Doyle et al., published Apr. 22, 1992, and PCT Patent Publication 91/12822, by Erfinder, published Sep. 5, 1991 intermediates. None of these references suggest the utility of phosphonosulfonate compounds, useful in preventing and treating bone metabolism disorders.

It has been surprisingly discovered that the compounds of the present invention, having a phosphonosulfonate moiety, may have potent bone antiresorptive activity and therapeutic utility in treating osteoporosis and/or arthritis. Moreover, these compounds have reduced bone affinity compared with bisphosphonates. This reduced bone affinity may decrease side effects generally associated with the high bone affinity bisphosphonates. Such side effects include inhibition of bone formation and inhibition of bone remodeling activation frequency.

Certain compounds of the present invention contain a quaternary nitrogen moiety. These compounds exhibit unusual solubility properties. Thus, the quaternary nitrogen-containing phosphonosulfonate compounds of the present invention may be more readily orally absorbed. Increased oral absorption allows for improved therapeutic effect at lower doses. Lower doses are generally preferable because undesirable side effects are decreased.

It is therefore an object of the present invention to provide a new potent class of compounds which are potent bone resorption inhibiting agents useful in osteoporosis therapy and anti-arthritic agents useful in the treatment of arthritis, especially osteoarthritis and rheumatoid arthritis. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or other mammals.

These and other objects of the present invention will become apparent from the detailed disclosure of the present invention provided hereinafter.

SUMMARY OF THE INVENTION

The present invention relates to phosphonosulfonates and the pharmaceutically-acceptable salts and esters thereof, having a structure according to formula (I):

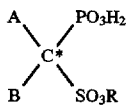

wherein (A)

(1) A is selected from the group consisting of hydrogen; halogen; $SR^1$; $R^2SR^1$; amino; hydroxy; and substituted or unsubstituted $C_1$–$C_8$ alkyl;

(2) B is (a) —$NH_2$;

(b) a saturated or unsaturated $C_1$–$C_{15}$ alkyl chain substituted with one or more substituents selected from the group consisting of —$R^3N(R^4)_2$; —$R^3$[—$N(R^5)_3$]+; —$R^3N(R^4)C(O)R^4$; —$R^3N(R^4)C(S)R^4$; —$R^3N(R^4)C(N)R^4$; and —$R^3C(O)N(R^4)_2$;

(c) a substituted or unsubstituted, saturated or unsaturated heteroalkyl chain having from 2 to 15 chain atoms, where one or more of said chain atoms is nitrogen;

(d) a saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3$[—$N(R^5)_3$]+; —$R^3N(R^4)C(O)R^4$; —$R^3N(R^4)C(S)R^4$; —$R^3N(R^4)C(N)R^4$; and —$R^3C(O)N(R^4)_2$; or (e) $R^6$—L— where (i) L is selected from the group consisting of nil; N; —$N(R^5)_2$+; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; $R^3$[—$N(R^5)_3$]+; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (3)

(a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;

(b) $R^2$ is substituted or unsubstituted $C_1$–$C_8$ alkyl;

(c) $R^3$ is selected from the group consisting of nil and substituted or unsubstituted $C_1$–$C_8$ alkyl;

(d) $R^4$ is independently selected from the group consisting of hydrogen; substituted or unsubstituted $C_1$–$C_8$ alkyl; and —$R^2SR^1$; and (e) $R^5$ is independently selected from the group consisting of substituted or unsubstituted $C_1$–$C_{15}$ alkyl; substituted or unsubstituted phenyl; benzyl; and —$R^2SR^1$;

or

A and B are covalently linked together with C* to form a monocyclic or bicyclic ring having the following structure:

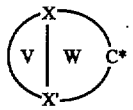

where
(1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C; except that if neither V nor W is a nitrogen containing heterocycle, then at least one of V or W is substituted with one or more substituents selected from the group consisting of $—R^3N(R^4)_2$; $R^3[—N(R^5)_3]+$; $—R^3N(R^4)C(O)R^4$; $—R^3N(R^4)C(S)R^4$; $—R^3N(R^4)C(N)R^4$; and $—R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl.

The present invention further relates to pharmaceutical compositions comprising a safe and effective amount of a phosphonosulfonate, or a pharmaceutically-acceptable salt or ester thereof. Finally, the present invention relates to methods for treating or preventing pathological conditions characterized by abnormal calcium and phosphate metabolism in humans or other mammals. These methods comprise administering to a human or other mammal in need of such treatment a safe and effective amount of a compound or a composition of the present invention.

DETAILED DESCRIPTION OF THE INVENTION

Phosphonosulfonate Compounds

The novel compounds of the present invention are phosphonosulfonates and the pharmaceutically-acceptable salts and esters thereof, having a structure according to formula (I):

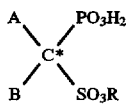

wherein
(A)
(1) A is selected from the group consisting of hydrogen; halogen; $SR^1$; $R^2SR^1$; amino; hydroxy; and substituted or unsubstituted $C_1$–$C_8$ alkyl;

(2) B is
(a) $—NH_2$;
(b) a saturated or unsaturated $C_1$–$C_{15}$ alkyl chain substituted with one or more substituents selected from the group consisting of $—R^3N(R^4)_2$; $—R^3[—N(R^5)_3]+$; $—R^3N(R^4)C(O)R^4$; $—R^3N(R^4)C(S)R^4$; $—R^3N(R^4)C(N)R^4$; and $—R^3C(O)N(R^4)_2$;

(c) a substituted or unsubstituted, saturated or unsaturated heteroalkyl chain having from 2 to 15 chain atoms, where one or more of said chain atoms is nitrogen;

(d) a saturated or unsaturated heteroalkyl chain having from 2 to 15 chain atoms, where one or more of said chain atoms is selected from S and O; and where said heteroalkyl chain is substituted with one or more substituents selected from the group consisting of $—R^3N(R^4)_2$; $—R^3[—N(R^5)_3]+$; $—R^3N(R^4)C(O)R^4$; $—R^3N(R^4)C(S)R^4$; $—R^3N(R^4)C(N)R^4$; and $—R^3C(O)N(R^4)_2$; or (e) $R^6$—L— where
(i) L is selected from the group consisting of nil; N; $—N(R^5)_2+$; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; $—R^3SR^1$; substituted or unsubstituted $C_1$–$C_8$ alkyl; $—R^3OR^4$; $—R^3CO_2R^4$; $—R^3O_2CR^4$; $—R^3N(R^4)_2$; $R^3[—N(R^5)_3]+$; $—R^3N(R^4)C(O)R^4$; $—R^3N(R^4)C(S)R^4$; $—R^3N(R^4)C(N)R^4$; $—R^3C(O)N(R^4)_2$; halogen; $—R^3C(O)R^4$; arylalkyl; nitro; substituted or unsubstituted aryl; and hydroxy; and (3)
(a) $R^1$ is independently selected from the group consisting of hydrogen; $—C(O)R^7$; $—C(S)R^7$; $—C(O)N(R^7)_2$; $—C(O)OR^7$; $—C(S)N(R^7)_2$; and $—C(S)OR^7$; where $R^7$ is hydrogen or substituted or unsubstituted $C_1$–$C_8$ alkyl;

(b) $R^2$ is substituted or unsubstituted $C_1$–$C_8$ alkyl;

(c) $R^3$ is selected from the group consisting of nil and substituted or unsubstituted $C_1$–$C_8$ alkyl;

(d) $R^4$ is independently selected from the group consisting of hydrogen; substituted or unsubstituted $C_1$–$C_8$ alkyl; and $—R^2SR^1$; and (e) $R^5$ is independently selected from the group consisting of substituted or unsubstituted $C_1$–$C_{15}$ alkyl; substituted or unsubstituted phenyl; benzyl; and $—R^2SR^1$;

or (B) A and B are covalently linked together with C* to form a monocyclic or bicyclic ring having the following structure:

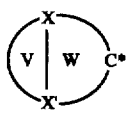

where (1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C; except that if neither V nor W is a nitrogen containing heterocycle, then at least one of V or W is substituted with one or more substituents selected from the group consisting of $-R^3N(R^4)_2$; $R^3[-N(R^5)_3]+$; $-R^3N(R^4)C(O)R^4$; $-R^3N(R^4)C(S)R^4$; $-R^3N(R^4)C(N)R^4$; and $-R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 15 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated or unsaturated, straight-chain or branched heteroalkyl chain, said chain having from 2 to 15, preferably 2 to 8 members, and comprising at least one carbon atom and at least one heteroatom. The term "heteroalkyl", as used herein, encompasses alkenyl heteroalkyl unsaturated chains having at least one olefinic double bond and alkynyl heteroalkyl unsaturated chains having at least one triple bond.

"Carbocyclic ring" or "Carbocycle" as used herein is an unsubstituted or substituted, saturated, unsaturated or aromatic, hydrocarbon ring. Carbocycles may be monocyclic or polycyclic: Monocyclic rings generally contain from 3 to 8 atoms, preferably 5 to 8 atoms. Polycyclic rings containing two rings contain 6–16, preferably 10 to 12, atoms and those with three rings generally contain 13 to 17, preferably 14 to 15, atoms.

"Heterocyclic ring" or "Heterocycle" as used herein is an unsubstituted or substituted, saturated, unsaturated or aromatic ring comprised of carbon atoms and one or more heteroatoms in the ring. Heterocyclic rings may be monocyclic or polycyclic. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms. Unless otherwise stated the heteroatoms may be independently chosen from nitrogen, sulfur, and oxygen. Unsaturated, non-aromatic heterocycles include, but are not limited to, substituted or unsubstituted thiophene, substituted or unsubstituted oxathiazole, substituted or unsubstituted pyrans, and substituted or unsubstituted furans.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl and hydroxypropyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH-alkyl-), such as aminomethyl alkyl.

"Alkylamino" is an amino moiety having one or two alkyl substituents (e.g., —N-alkyl), such as dimethylamino.

"Alkenylamino" is an amino moiety having one or two alkenyl substituents (e.g., —N-alkenyl).

"Alkynylamino" is an amino moiety having one or two alkynyl substituents (e.g., —N-alkynyl).

"Alkylimino" is an imino moiety having one or two alkyl substituents (e.g., —N-alkyl-).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, e.g. R—C(=O). Preferred acyl groups include, but are not limited to, acetyl, propionyl, butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein the term "thio-substituent" ($SR^1$ or $R^2SR^1$) includes thiols [—SH] where $R^1$=H; thioesters [—SC(O)$R^7$] where $R^1$=C(O)$R^7$; dithioesters [—SC(S)$R^7$] where $R^1$=C(S)$R^7$; thiocarbamates [—SC(O)N($R^7$)$_2$] where $R^1$=C(O)N($R^7$)$_2$; dithiocarbamates [—SC(S)N($R^7$)$_2$] where $R^1$=C(S)N($R^7$)$_2$; thiocarbonates [—SC(O)O$R^7$] where $R^1$=C(O)O$R^7$; and dithiocarbonates [—SC(S)O$R^7$] where $R^1$=C(S)O$R^7$. $R^7$ is a hydrogen or $C_1$-$C_8$ alkyl. Any of the $SR^1$ substituents may themselves be substituted with an $R^2$ moiety, where $R^2$ is a substituted or unsubstituted $C_1$-$C_8$ alkyl. Accordingly, additional thio-substituents denoted by $R^2SR^1$ are alkylthiols, alkylthioesters, alkyldithioesters, alkylthiocarbamates, alkyldithiocarbamates, alkylthiocarbonates and alkyl dithiocarbonates.

The term "phosphonosulfonate", as used herein, relates to compounds that have a phosphonate group (PO$_3$H$_2$) and a sulfonate group (SO$_3$H) attached to the same carbon atom.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride), acetate and phosphate salts.

A "biohydrolyzable ester" is an ester of the phosphonosulfonate compounds that does not interfere with the therapeutic activity of the compounds, or that is readily metabolized by a human or other mammal. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyl oxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). While the preceding esters are preferred, any pharmaceutically-acceptable ester is deemed to be within the scope of the present invention.

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, thioxo (—C(=S)—); amino, aminoalkyl (e.g. aminomethyl, etc.), cyano, quaternary amino, quaternary aminoalkyl, amidino, amidinoalkyl, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, hydroxyalkyl, aryloxy, arylalkyl, alkynyl and combinations thereof. Particularly preferred substituents include, but are not limited to, amino, aminoalkyl, quaternary amino, amidino, quaternary aminoalkyl and amidinoalkyl.

Also, as used in defining the structure of the compounds of this invention, a particular radical may be defined for use as a substituent, in multiple locations. As used herein, such a radical is independently selected each time it is used.

In formula (I), when A is halogen, it is preferably chlorine or bromine. When A is a sulfur containing moiety, the preferred moiety is $SR^1$, where $R^1$ is preferably hydrogen or acyl. Particularly preferred is where $R^1$ is hydrogen. Preferred A moieties are amino and hydroxy. Particularly preferred is where A is hydroxy. When B is saturated or unsaturated $C_1$-$C_{15}$ alkyl, the alkyl chain must be substituted with one or more substituents selected from the group consisting of —$R^3$N($R^4$)$_2$; $R^3$[—N($R^5$)$_3$]+; —$R^3$N($R^4$)C(O)$R^4$; —$R^3$N($R^4$)C(S)$R^4$; —$R^3$N($R^4$)C(N)$R^4$; and —$R^3$C(O)N($R^4$)$_2$. Preferably the required substituent is selected from —$R^3$N($R^4$)$_2$; $R^3$[—N($R^5$)$_3$]+; —$R^3$N($R^4$)C(O)$R^4$; —$R^3$N($R^4$)C(S)$R^4$; and —$R^3$N($R^4$)C(N)$R^4$. Most preferred is where the required substituent is selected from —$R^3$N($R^4$)$_2$; $R^3$[—N($R^5$)$_3$]+; and —$R^3$N($R^4$)C(O)$R^4$. The alkyl chain may also be substituted with one or more substituents selected from the group consisting of nil; —$R^3SR^1$; hydrogen; substituted or unsubstituted $C_1$-$C_8$ alkyl; —$R^3OR^4$; —$R^3CO_2R^4$; —$R^3O_2CR^4$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred are $C_1$-$C_8$ alkyl chains.

When B is saturated or unsaturated heteroalkyl having from 2 to 15 atoms, where one of said atoms is a nitrogen, the heteroalkyl chain may be substituted with one or more substituents selected from the group consisting of —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)_2$; —$R^3$[N($R^5$)$_3$]+; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred nitrogen-containing heteroalkyl chains have from 2 to 8 chain atoms.

When B is saturated or unsaturated heteroalkyl having from 2 to 15 atoms, where one of said atoms is a sulfur or oxygen, and where no nitrogen atom is in the heteroalkyl chain, then the heteroalkyl chain must be substituted with one or more substituents selected from the group consisting of —$R^3N(R^4)_2$; $R^3$[—N($R^5$)$_3$]+; —$R^3N(R^4)C(O)R^4$; —$R^3N(R^4)C(S)R^4$; —$R^3N(R^4)C(N)R^4$; and —$R^3C(O)N(R^4)_2$. The required substituent is preferably one of —$R^3N(R^4)_2$; $R^3$[—N($R^5$)$_3$]+; —$R^3N(R^4)C(O)R^4$; —$R^3N(R^4)C(S)R^4$; or —$R^3N(R^4)C(N)R^4$. Most preferred is where the required substituent is —$R^3N(R^4)_2$; $R^3$[—N($R^5$)$_3$]+; or —$R^3N(R^4)C(O)R^4$. The heteroalkyl chain may also be substituted with one or more substituents selected from the group consisting of nil; —$R^3SR^1$; hydrogen; substituted or unsubstituted $C_1$-$C_8$ alkyl; —$R^3OR^4$; —$R^3CO_2R^4$; —$R^3O_2CR^4$; halogen;

—$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred non-nitrogen containing heteroalkyl chains have from 2 to 8 chain atoms.

When B is $R^6$—L—, the L moiety may be substituted with one or more substituents selected from the group consisting of —$R^3SR^1$; hydrogen; substituted or unsubstituted $C_1$–$C_8$ alkyl; —$R^3OR^4$; —$R^3CO_2R^4$; —$R^3O_2CR^4$; —$R^3N(R^4)_2$; —$R^3[N(R^5)_2]+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. The L moiety is preferably a nitrogen atom (including quaternary nitrogen), a nitrogen containing heteroalkyl, or alkyl. Where L is a heteroalkyl chain or an alkyl chain, the chain preferably has 1 to 8 chain atoms.

The $R^6$ moiety may be a saturated or unsaturated, monocyclic or polycyclic carbocycle or heterocycle. Where $R^6$ is a monocyclic carbocycle, it is preferably cycloheptyl or cyclohexyl. When $R^6$ is a monocyclic heterocycle, preferred are six-membered nitrogen containings rings including pyridine, pyrimidine, piperidine. Also preferred are those six-membered heterocycles having a quaternary nitrogen ring atom, including pyridinium, pyrimidinium, piperidinium, and pyrazolium. Preferred monocyclic heterocycles also include five-membered nitrogen containing heterocycles, including imidazol, pyrrole, and pyrrolidine. Also preferred are five-membered heterocycles having a quaternary nitrogen ring atom, including imidazolium, pyrrolium, and pyrrolidinium. Where $R^6$ is a polycycle, preferred are polycyclic heterocycles having a six-membered ring fused to another six-membered ring and those having a six-membered ring fused to a five-membered ring. Preferred polycyclic heterocycles include those having a quaternary ring nitrogen atom. Particularly preferred $R^6$ moieties include pyridyl and cycloheptyl.

The $R^3$ moiety is preferably nil.

The $R^4$ moiety is preferably hydrogen.

The $R^5$ moiety comprises a nitrogen atom bound to three carbon-containing moieties. The $R^5$ moiety is substituted on a carbon atom of another moiety, thus providing a quaternary amine group. As indicated in the general structure, the quaternary amine moiety may be a substituent on any of the chain or cyclic moieties described above.

B is preferably a heteroalkyl chain having at least one nitrogen chain atom, or $R^6$—L—. Particularly preferred B moieties are $R^6$—L—.

According to formula (I), A and B may, together with C*, X and X', form a cyclic structure. Preferred cyclic structures are those where V is a heterocycle having at least one ring nitrogen atom. This ring nitrogen atom may be a secondary, tertiary or quaternary amine. Where neither V nor W is a heterocycle having at least one ring nitrogen atom, then at least one of V or W must be substituted with one or more moieties selected from the group consisting of —$R^3N(R^4)_2$; $R^3[—N(R^5)_3]+$; —$R^3$—$N(R^4)C(O)R^4$; —$R^3N(R^4)C(S)R^4$; —$R^3N(R^4)C(N)R^4$; and —$R^3C(O)N(R^4)_2$. In addition to the above requirement, each of V and W may be substituted with one or more substituents selected from the group consisting of —$R^3SR^1$; hydrogen; substituted or unsubstituted $C_1$–$C_8$ alkyl; —$R^3OR^4$; —$R^3CO_2R^4$; —$R^3O_2CR^4$; halogen; —$R^3C(O)R^4$; hydroxy; substituted or unsubstituted arylalkyl; nitro; and unsubstituted or substituted aryl.

Preferred compounds of the present invention are phosphono-sulfonates and the pharmaceutically-acceptable salts and esters thereof, having a general structure according to formula (I):

wherein (A)
(1) A is selected from the group consisting of amino and hydroxy; and
(2) B is

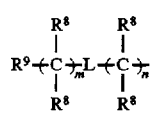

wherein (a) m is an integer from 0 to 10; n is an integer from 0 to 10; and m+n is an integer from 0 to 10;
(b) $R^8$ is independently selected from the group consisting of nil; —$R^3SR^1$; hydrogen; substituted or unsubstituted $C_1$–$C_8$ alkyl; —$R^3OR^4$; —$R^3CO_2R^4$; —$R^3O_2CR^4$; —$R^3N(R^4)_2$; —$R^3[N(R^5)_3]+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings;
(c) $R^1$ is independently selected from the group consisting of hydrogen; —C(O)$R^7$; —C(S)$R^7$; —C(O)N($R^7$)$_2$; —C(O)O$R^7$; —C(S)N($R^7$)$_2$; and —C(S)O$R^7$; where $R^7$ is hydrogen or substituted or unsubstituted $C_1$–$C_8$ alkyl;
(d) $R^3$ is selected from the group consisting of nil and substituted or unsubstituted $C_1$–$C_8$ alkyl;
(e) $R^4$ is independently selected from the group consisting of hydrogen; substituted or unsubstituted $C_1$–$C_8$ alkyl; and —$R^2SR^1$;
(f) $R^5$ is independently selected from the group consisting of substituted or unsubstituted $C_1$–$C_{15}$ alkyl; substituted or unsubstituted phenyl; benzyl; and —$R^2SR^1$;
(g) L is selected from the group consisting of nil; —N($R^8$)—; [—N($R^5$)$_2$—]+; —S—; —O—; and —D—C(=E)—S—, where D is selected from the group consisting of covalent bond, O, or S, and E is O or S; and wherein
(i) when L is —N($R^8$)—, or when L is [—N($R^5$)$_2$—]+ and m is an integer from 1 to 10, $R^9$ is independently selected from the group consisting of nil; hydrogen; substituted or unsubstituted $C_1$–$C_{15}$ alkyl; $R^2SR^1$; and $R^{10}$;
(ii) when L is [—N($R^5$)$_2$—]+ and m=0, $R^9$ is selected from the group consisting of substituted or unsubstituted $C_1$–$C_{15}$ alkyl; $R^2SR^1$; and $R^{10}$; or (iii) when L is nil, —S—, —O—, or —D—C(=E)
—S, $R^9$ is $R^{10}$;

(h) $R^{10}$ is a saturated, unsaturated, or aromatic monocyclic or polycyclic carbocycle or a saturated, unsaturated, or aromatic monocyclic or polycyclic heterocycle containing one or more heteroatoms; where said carbocycle or heterocycle is substituted with one or more $R^{11}$ substituents; and (i) each $R^{11}$ is independently selected from the group consisting of —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)_2$; $R^3[-N(R^5)_3]+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; hydroxy; substituted or unsubstituted arylalkyl; nitro; and unsubstituted or substituted aryl;

or (B) A and B are covalently linked together with C* to form a monocyclic or bicyclic ring having the following structure:

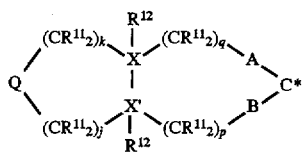

wherein (a) A and B are independently selected from the group consisting of nil, —O—, —S—, and —$NR^{12}$—;

(b) Q is selected from the group consisting of nil; —$NR^{12}$—; and [—$N(R^{13})_2$—]+;

(c) X and X' are independently selected from C or N;

(d) each $R^{12}$ is independently selected from the group consisting of nil; —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)_2$; $R^3[-N(R^5)_3]+$; —$R^3N(R^4)C(O)R^4$; —$R^3C(O)N(R^4)_2$; halogen; —$R^3C(O)R^4$; hydroxy; substituted or unsubstituted arylalkyl; nitro; and unsubstituted or substituted aryl; and (e) each $R^{13}$ is selected from the group consisting of substituted or unsubstituted $C_1$-$C_{15}$ alkyl; substituted or unsubstituted phenyl; benzyl; and —$R^2SR^1$;

(f) When Q is other than nil, k and j and k+j are integers from 0 to 5; when Q is nil, k and j and k+j are integers from 0 to 6; and (g) p and q and p+q are independently integers from 0 to 3; except that if Q is nil, then at least one of $R^{11}$ or $R^{12}$ is selected from the group consisting of —$R^3N(R^4)_2$; $R^3[-N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl.

Preferred phosphonosulfonate compounds of formula (I) have a nitrogen containing heterocycle linked to the phosphonosulfonate geminal carbon via a linking chain. Included are phosphonosulfonate compounds having the following general structures:

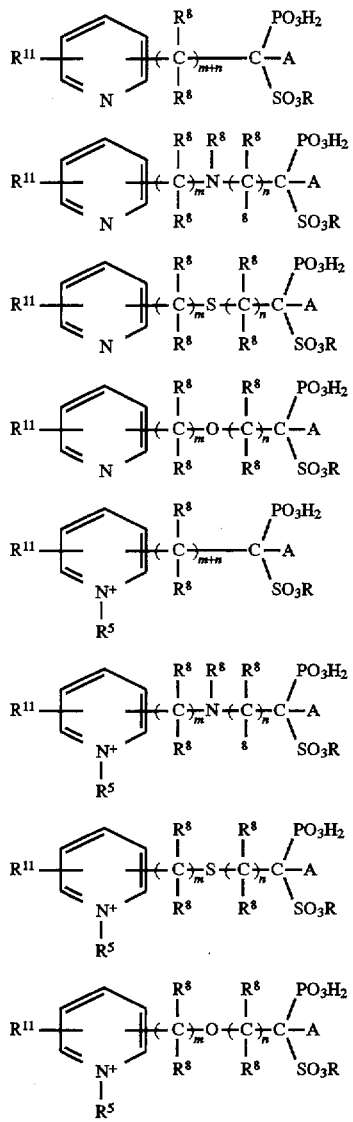

where the nitrogen containing heterocycle is a pyridyl or pyridinium;

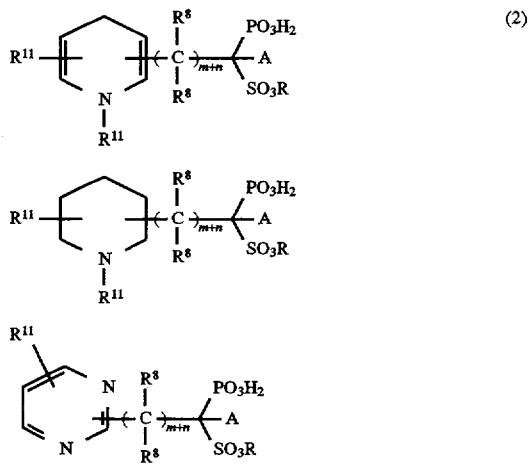

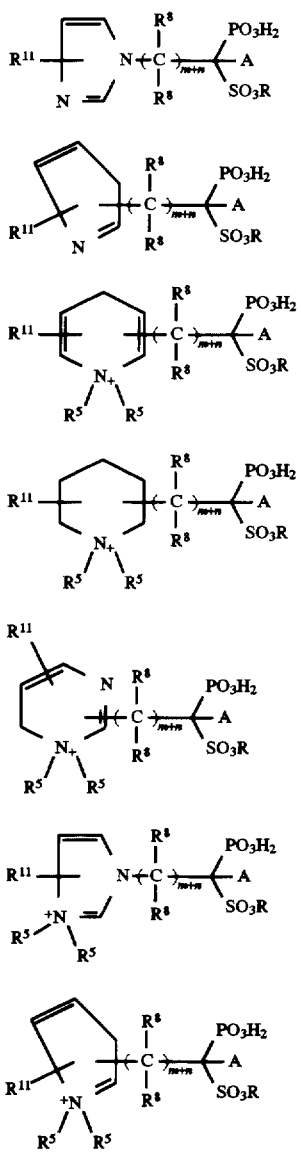

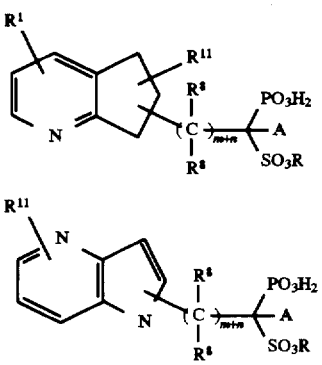

where the nitrogen containing heterocycle is a monocycle other than pyridyl or pyridinium;

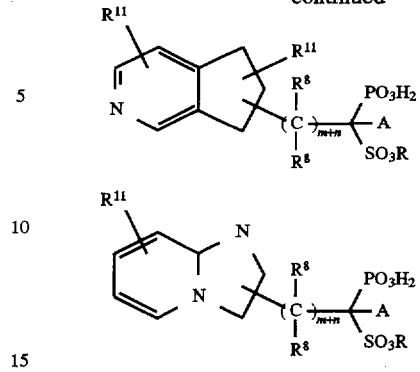

where the nitrogen containing heterocycle is a polycycle.

Also preferred are those phosphonosulfonate compounds having a nitrogen containing heteroalkyl moiety linked to the phosphonosulfonate containing geminal carbon. Such compounds include those having the following structure, where $R^8$ and $R^9$ are non-cyclic substituents:

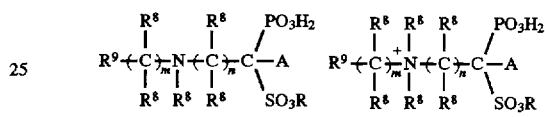

Also preferred are those compounds having the following structure, where $R^9$ is a cycloheptyl ring:

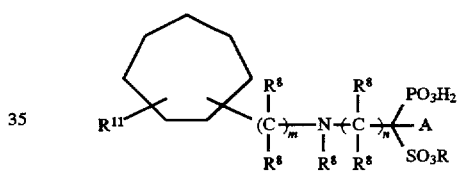

Also preferred are substituted or unsubstituted octahydro phosphonosulfono pyrindines having the general structures:

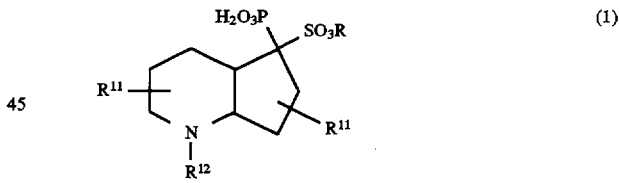

referred to herein as unsubstituted or substituted octahydro-5-phosphono-5-sulfono-1-pyrindines;

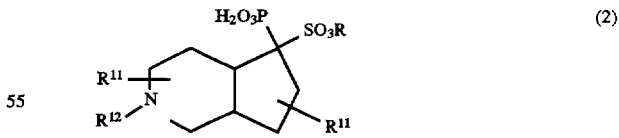

referred to herein as unsubstituted or substituted octahydro-5-phosphono-5-sulfono-2-pyrindines;

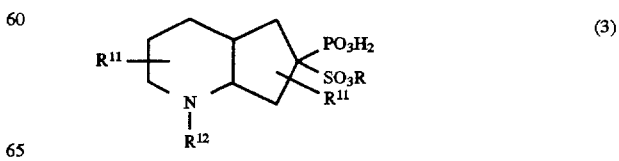

referred to herein as unsubstituted or substituted octahydro-6-phosphono-6-sulfono-1-pyrindines;

(4)

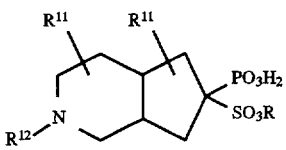

referred to herein as unsubstituted or substituted octahydro-6-phosphono-6-sulfono-2-pyrindines;

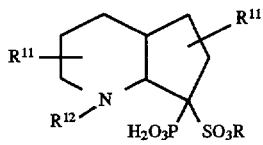
(5)

referred to herein as octahydro-7-phosphono-7-sulfono-1-pyrindines;

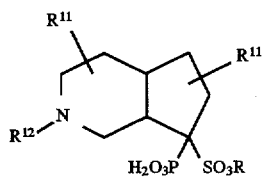
(6)

referred to herein as octahydro-7-phosphono-7-sulfono-2-pyrindines;

Also preferred are substituted or unsubstituted octahydro phosphonosulfono pyrindiniums having the general structures:

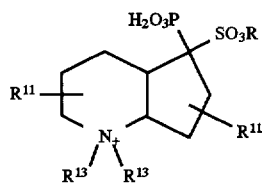
(1)

referred to herein as octahydro-5-phosphono-5-sulfono-1-pyrindinium;

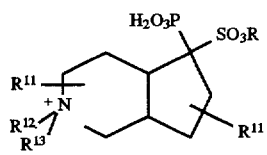
(2)

referred to herein as octahydro-5-phosphono-5-sulfono-2-pyrindinium;

(3)

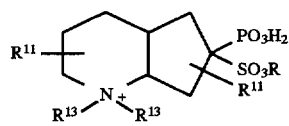

referred to herein as octahydro-6-phosphono-6-sulfono-1-pyrindinium;

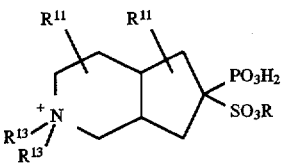
(4)

referred to herein as octahydro-6-phosphono-6-sulfono-2-pyrindinium;

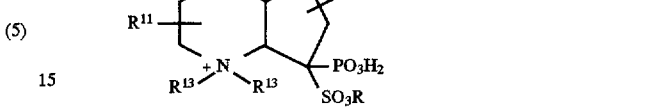
(5)

referred to herein as octahydro-7-phosphono-7-sulfono-1-pyrindinium; and

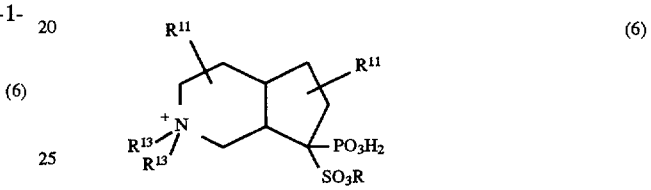
(6)

referred to herein as octahydro-7-phosphono-7-sulfono-2-pyrindinium.

Specific examples of compounds of the present invention are:

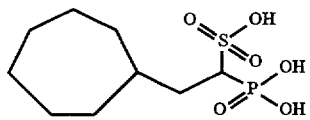

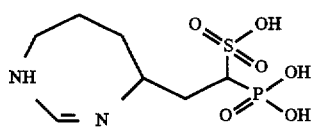

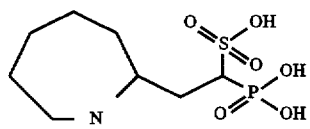

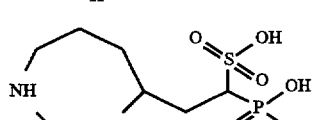

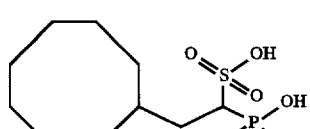

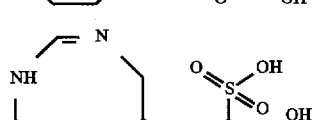

-continued
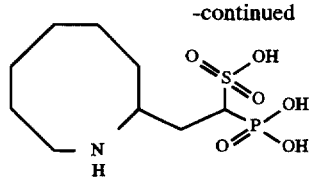
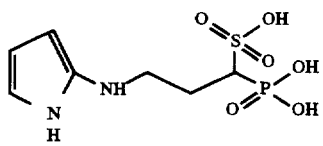
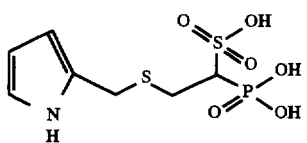
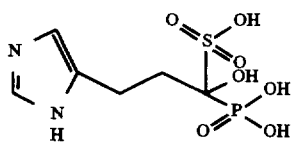
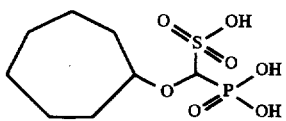
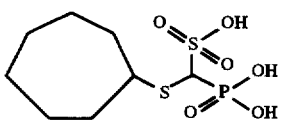
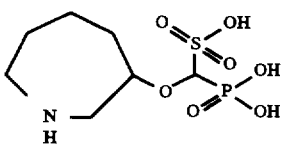
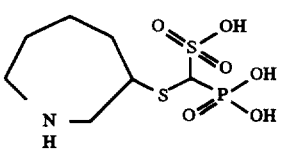
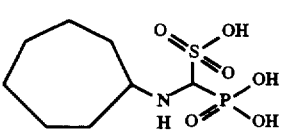
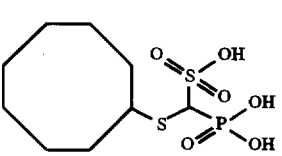
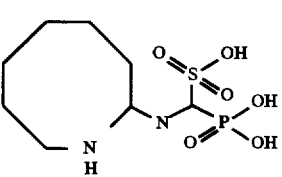
-continued
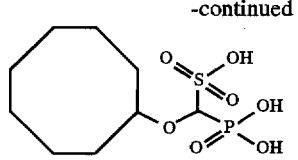
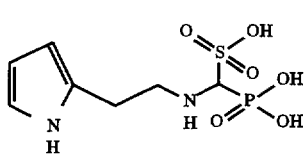
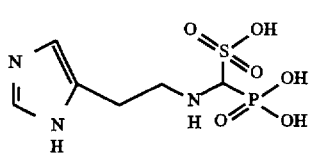
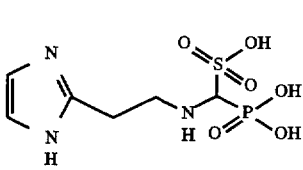
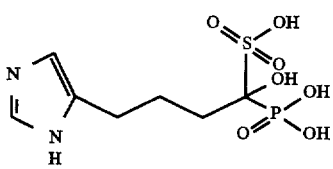
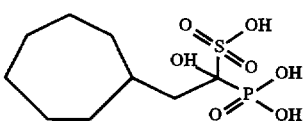
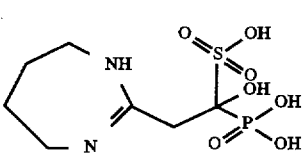
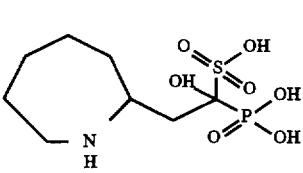
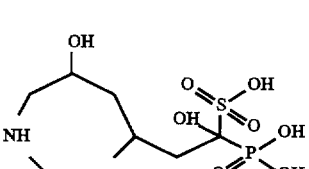
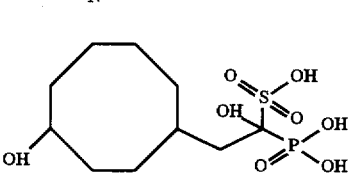

-continued
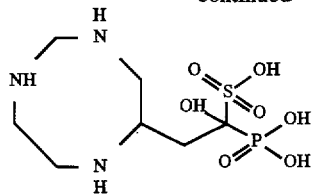
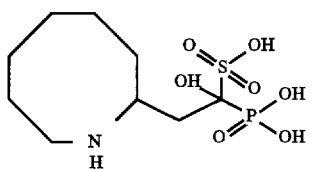
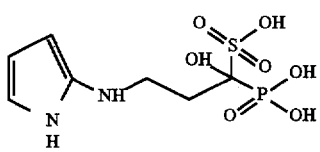
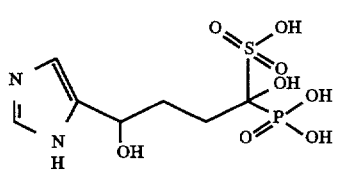
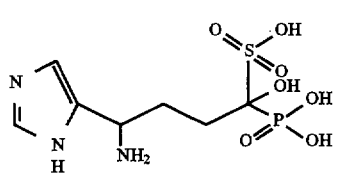
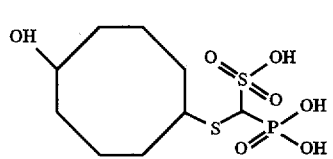
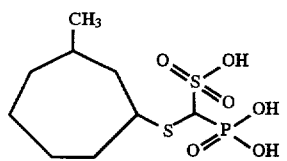
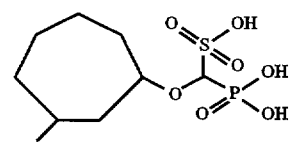
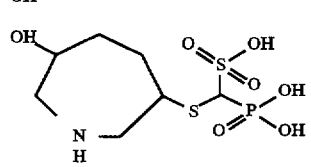
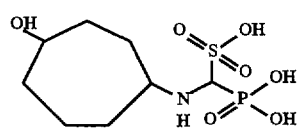
-continued
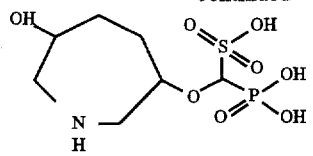
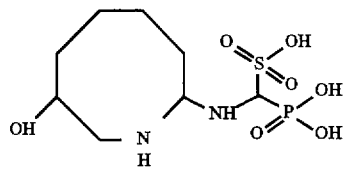
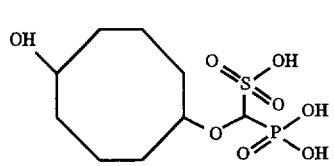
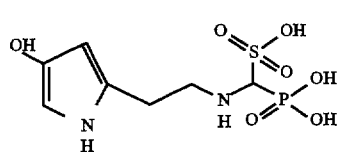
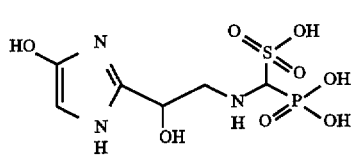
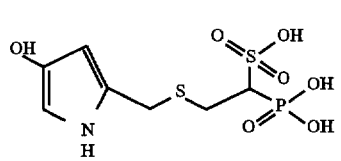
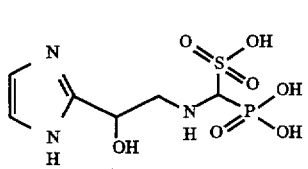
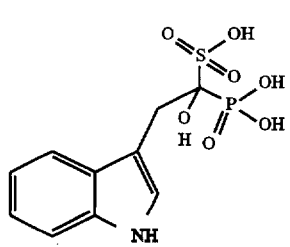
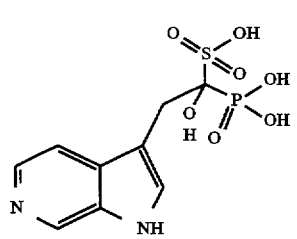

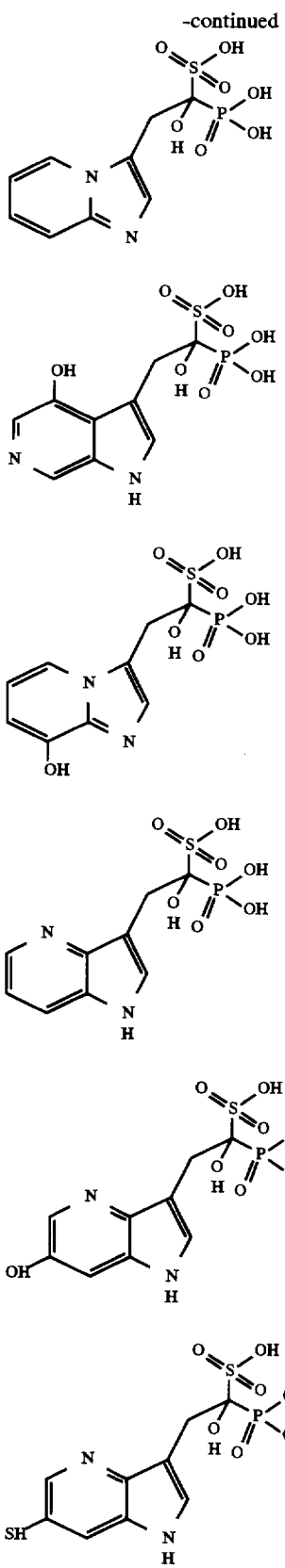
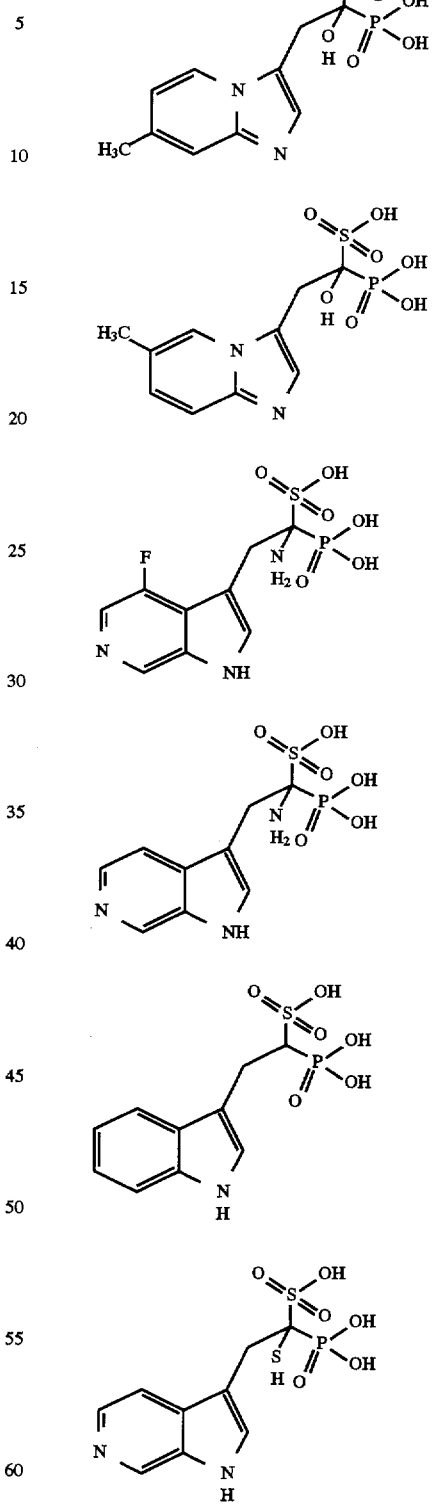

-continued
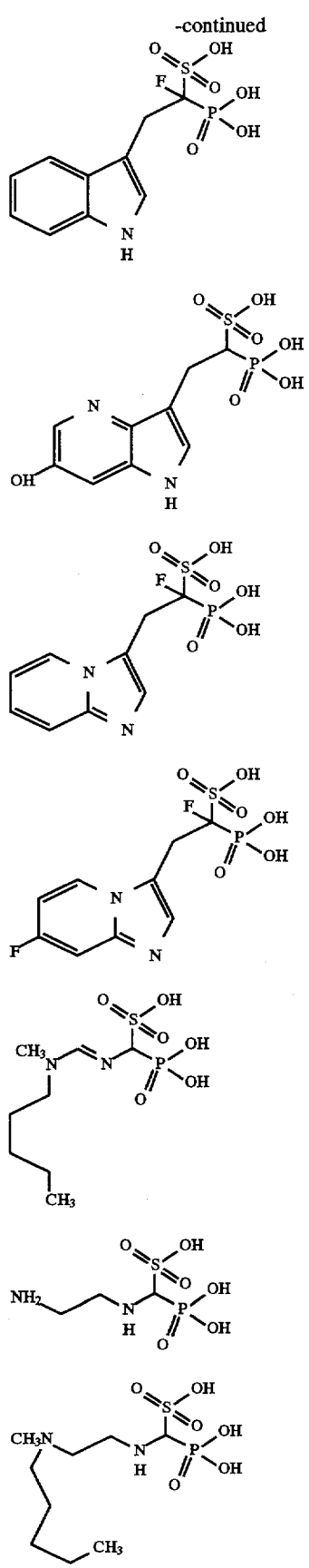
-continued
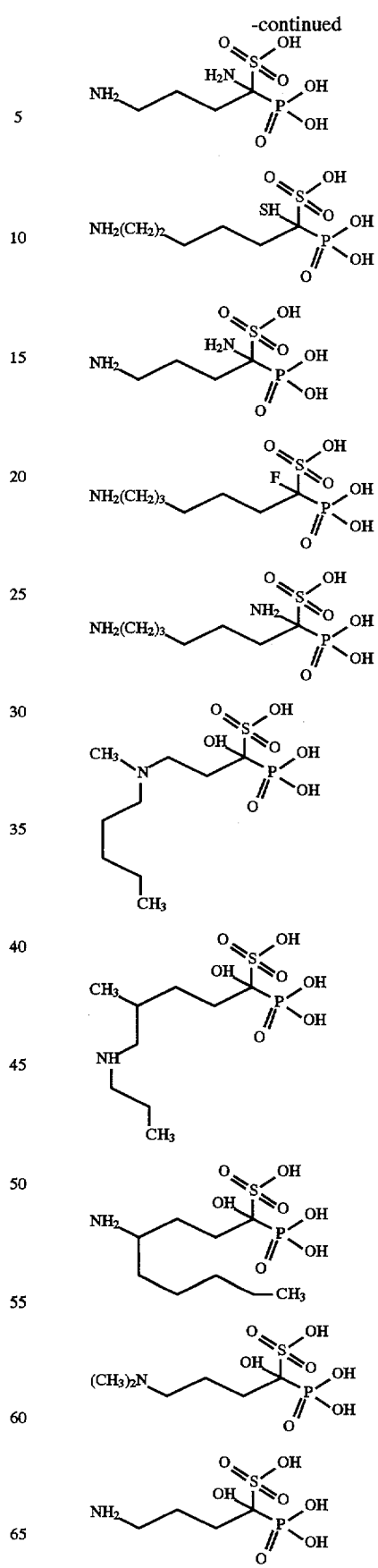

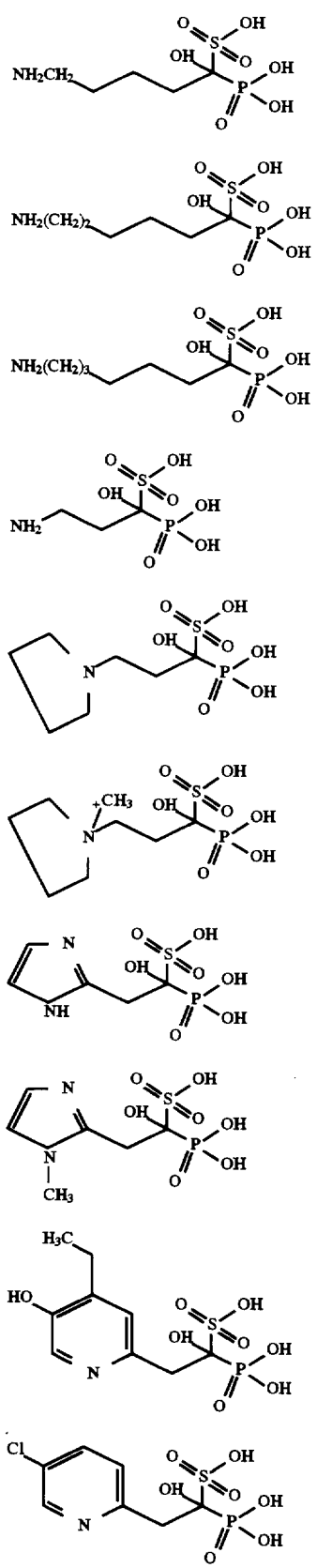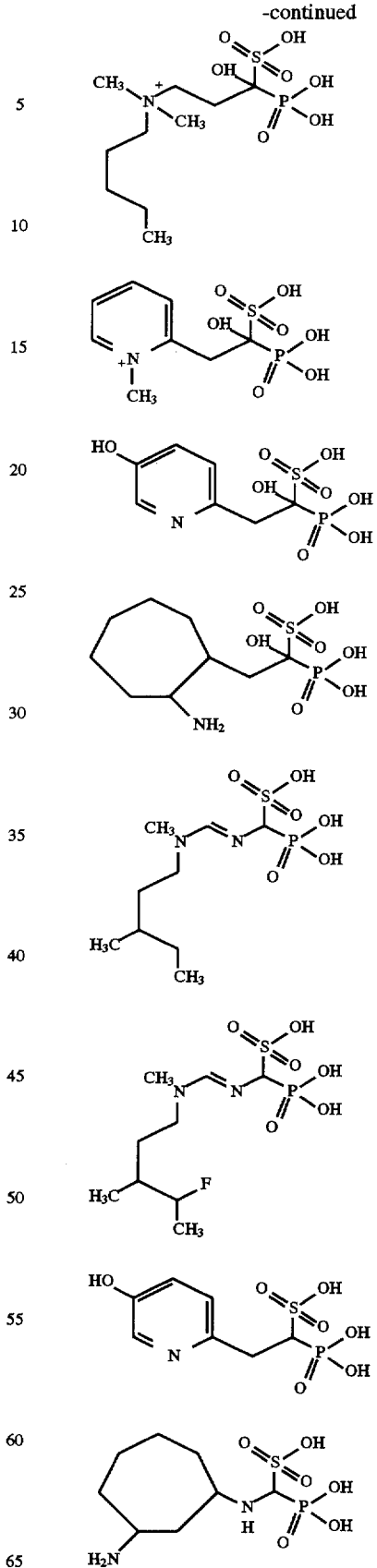

-continued
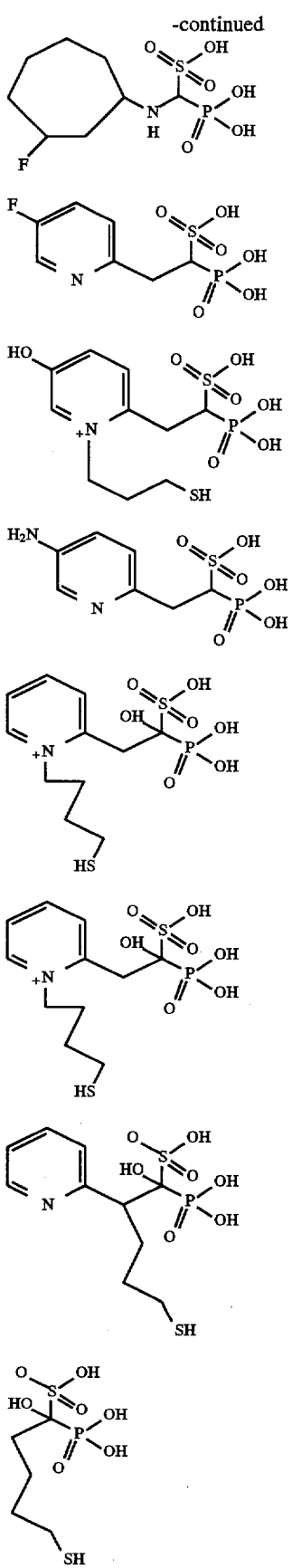
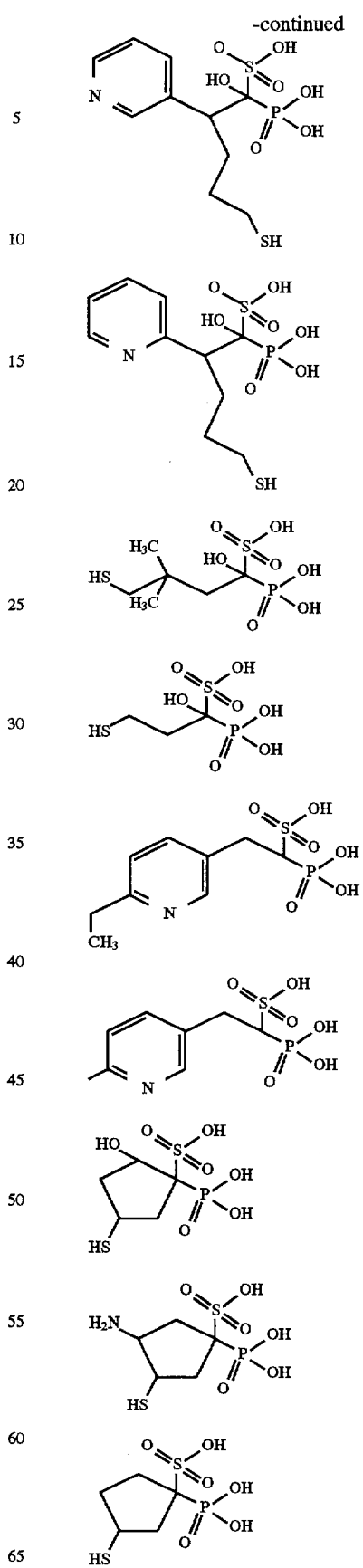

-continued
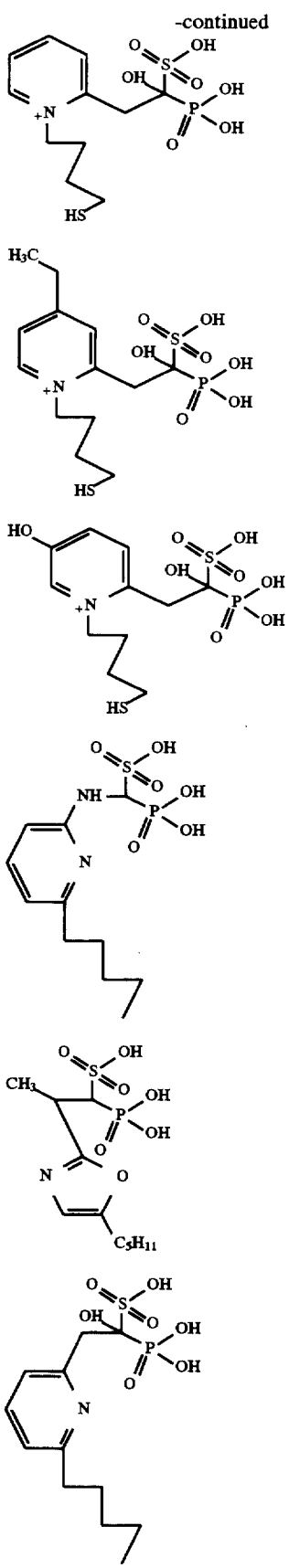
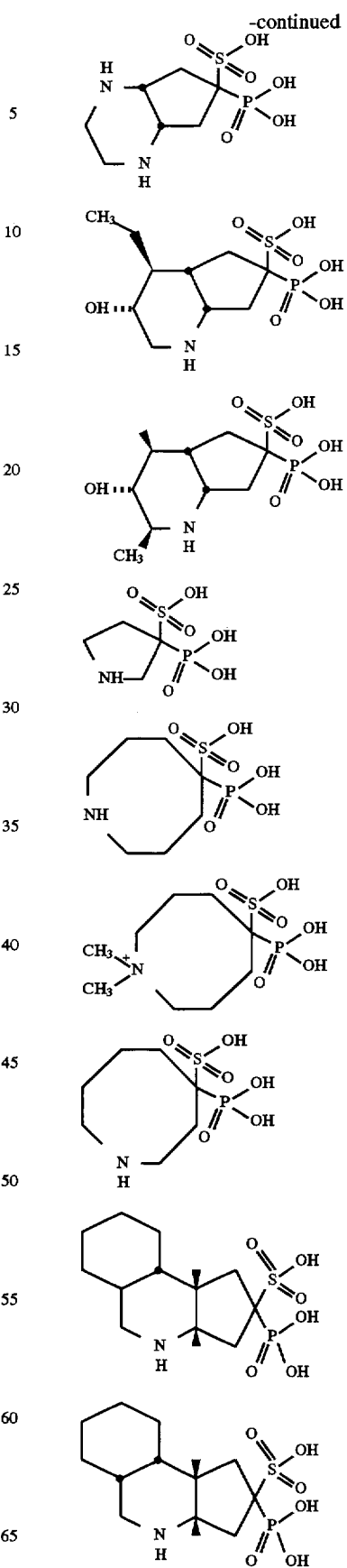

33
-continued
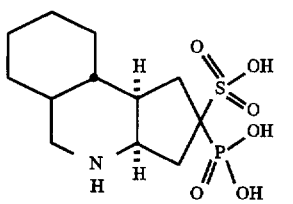
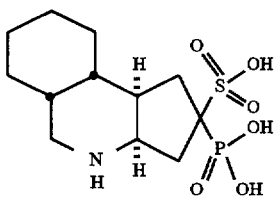
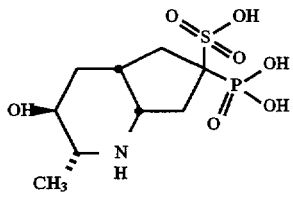
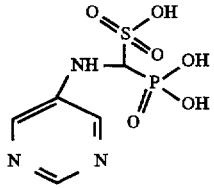
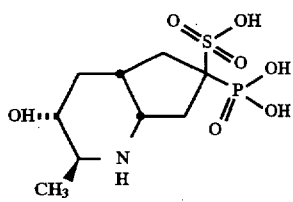
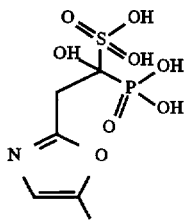
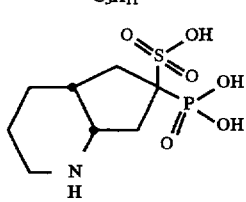
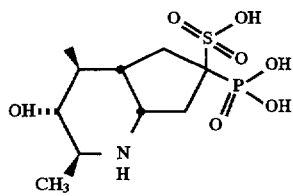
34
-continued
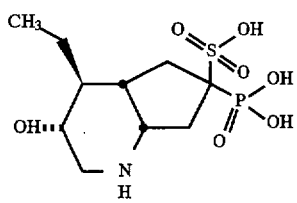
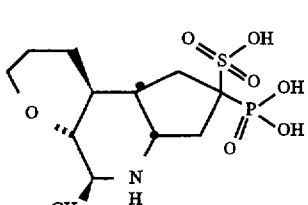
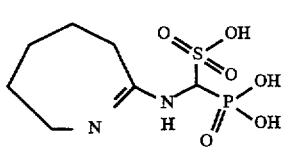
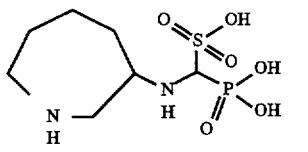
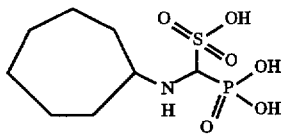
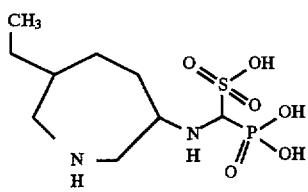
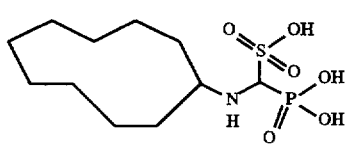
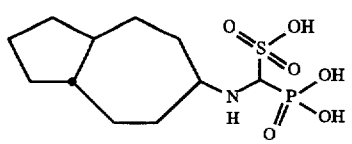
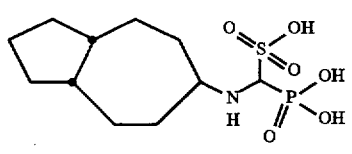

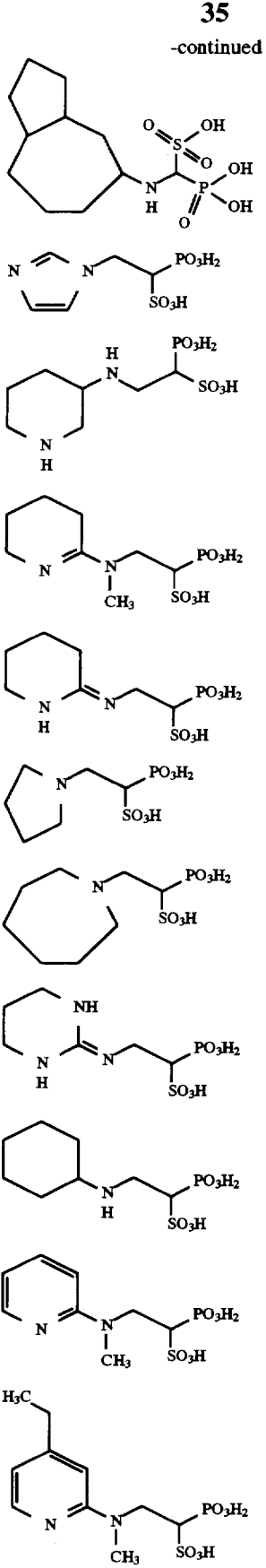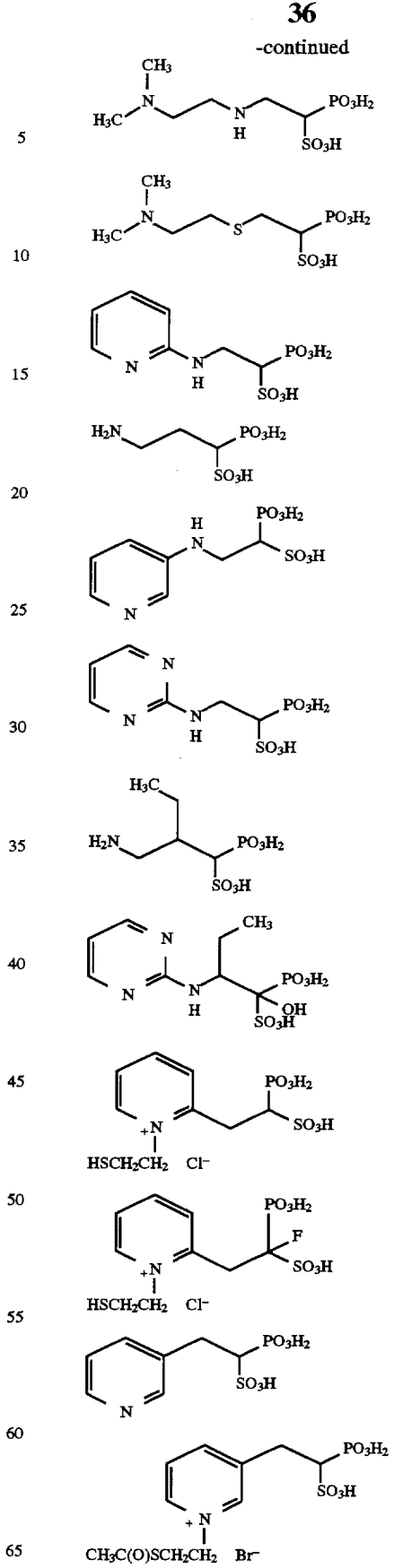

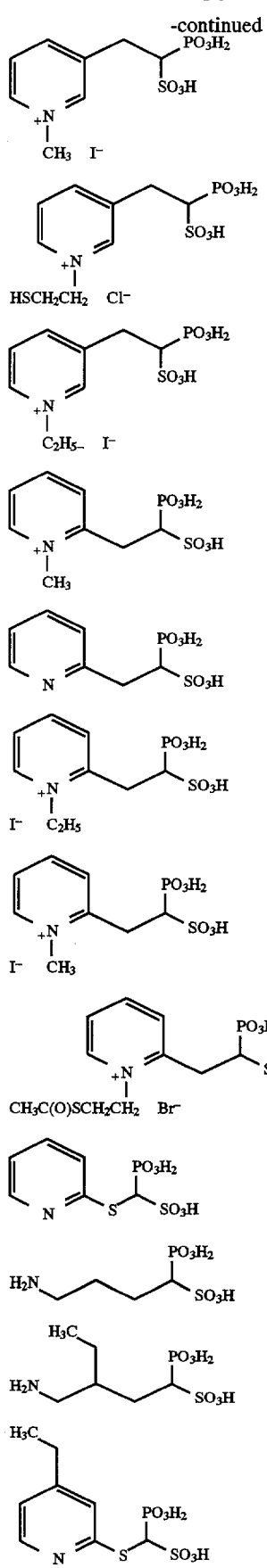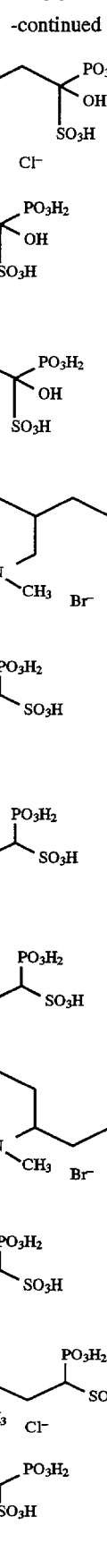

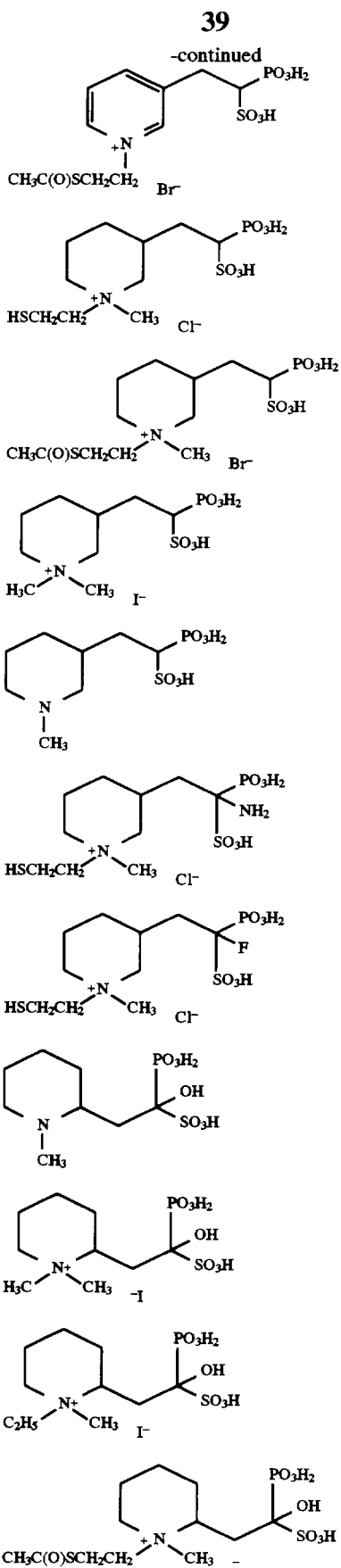
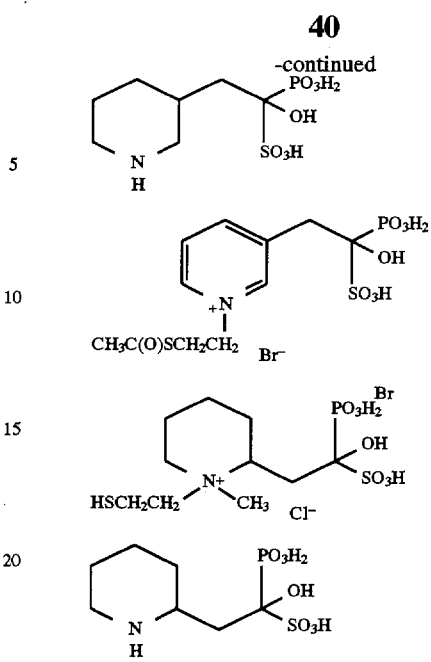

and the pharmaceutically-acceptable salts and esters thereof.

The term "pharmaceutically-acceptable salts and esters", as used herein, means hydrolyzable esters and salts of the phosphonosulfonate compounds which have the same general pharmacological properties as the acid form from which they are derived, and which are acceptable from a toxicity viewpoint. Pharmaceutically acceptable salts include alkali metals (e.g., sodium and potassium), alkaline earth metals (e.g., calcium and magnesium), non-toxic heavy metals (e.g., stanous and indium), and ammonium and low molecular weight substituted ammonium (e.g., mono-, di- and triethanolamine) salts. Preferred compounds are the sodium, potassium, and ammonium salts.

In order to determine and assess pharmacological activity, testing of the phosphonosulfonate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. One such test known to those skilled in the an is the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,683,080, to Francis, issued Aug. 8, 1972; U.S. Pat. No. 4,134,969, to Schmidt-Dunker, issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di-(e.g. calcium and magnesium) and trivalent (e.g. indium) metal ions. Thus, the compounds of the present invention are useful as builders in detergents and cleansers, or for treating water. They are also useful as stabilizers for compounds. In addition, they may be useful in preventing the formation of tartar (i.e., calculus) and/or plaque on teeth. Finally, the compounds of the present invention may be useful as herbicides which are nontoxic to animals.

The phosphonosulfonate compounds of the present invention are prepared from commercially-available materials according to non-limiting Examples 1 to 61. Generally, the synthesis reaction may be carried out in the following way: In a first step, a compound containing a carbon geminally substituted with a phosphono group and a sulfono group (for example methyl 1-dimethoxyphosphinylethenesulfonate or diethoxyphosphinylmethanesulfonate lithium salt) is coupled with a second compound to produce a product with a new group off of the geminally substituted carbon. If so desired, the geminally substituted carbon can be hydroxylated in a second step. In a third step, any phosphonic and sulfonic esters are removed. In a fourth step, if saturated heterocyclic rings are desired, hydrogenation is carried out. If quaternary amines are desired, these may be produced in a fifth step by reaction with alkylating reagents. Finally, if different salts are desired these may be prepared, for example, by conversion with ion exchange resins in the proper salt form.

Compositions Containing Novel Phosphonosulfonate Compounds

The phosphonosulfonate compounds of the present invention may be administered to humans or other mammals by a variety of routes, including, but not limited to, oral dosage forms and injections (intravenous, intramuscular, intraperitoneal and subcutaneous). Numerous other dosage forms containing the novel phosphonosulfonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the phosphonosulfonate compound active ingredient; or mixtures thereof, and pharmaceutically-acceptable excipients.

The phrase "safe and effective amount", as used herein, means an amount of a compound or composition great enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular phosphonosulfonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Accordingly, the pharmaceutical compositions of the present invention include from 15–95% of a phosphonosulfonate compound active ingredient, or mixture, thereof, 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described here in Examples 62–64. It is well within the capabilities of one skilled in the art to vary the non-limiting examples described herein to achieve a broad range of pharmaceutical compositions.

The choice of a pharmaceutically-acceptable excipient to be used in conjunction with the phosphonate compounds of the present invention is basically determined by the way the phosphonate compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The pharmaceutically-acceptable carrier employed in conjunction with the phosphonosulfonate compounds of the present invention is used at a concentration sufficient to provide a practical size to dosage relationship. The pharmaceutically-acceptable carriers, in total, may comprise from 0.1% to 99.9% by weight of the pharmaceutical compositions of the present invention, and preferably from 20% to 80%.

The preferred mode of administering the phosphonosulfonate compound of the present invention is orally. The preferred unit dosage form is therefore tablets, capsules and the like, comprising a safe and effective amount of the phosphonate compound of the present invention. Preferably, the compositions comprise from about 1 mg P to about 600 mg P of a phosphonosulfonate compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorus atom present in an amount of a phosphonosulfonate compound of the present invention. This unit is used to standardize the amount of the phosphonosulfonate compounds of the present invention to be used in the pharmaceutical compositions and methods of the present inventions. For example, 1-hydroxy-1-phosphono-2-(3-pyridinyl) ethanesulfonic acid has a molecular weight of 283 g/mole, of which 11% (31 g/mole) is due to the phosphorus atom present in this molecule. One milligram of this compound is therefore calculated to have 0.11 mg P. Thus, to prepare a pharmaceutical composition containing 0.11 mg P of this compound, the composition should contain 1 mg of the compound; and to dose 0.11 mg P/kg of this compound to a 50 kg patient, the patient would be dosed with 50 mg of this compound.

The rate of systemic delivery can be satisfactorily controlled by one skilled in the art, by manipulating any one or more of the following:

(a) the active ingredient;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different phosphonosulfonate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic adds and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropyl methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of a phosphonosulfonate compound of the present invention.

The preferred mode of administration is oral, but other known methods of administration are contemplated as well, e.g., dermato mucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and sub cutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis, osteoarthritis, neuritis, bursitis, tendonitis and other inflammatory conditions which predispose involved tissue to deposition of calcium phosphates.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anticonvulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteopetrosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium phosphate.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of phosphonosulfonate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from 0.01 mg P to 3500 mg P, or from 0.0002 to 70 mg P/kg of body weight (based on a body weight of 50 kg). Preferred single dosages are from 1 mg P to 600 mg P, or from 0.02 to 12 mg P/kg of body weight (based on a body weight of 50 kg). Up to four single dosages per day may be administered. Daily dosages greater than 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of 2-(1-Imidazolyl)-1-phosphonoethanesulfonic Acid

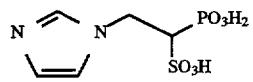

A mixture of 0.68 g (0.01 mole) of imidazole and 2.30 g (0.01 mole) of methyl 1-dimethoxyphosphinylethenesulfonate (U.S. Pat. No. 5,011,938 issued to Barnett et al. on Apr. 30, 1991) in 20 ml of chloroform is stirred at 20°–50° for one day. The reaction is cooled to room temperature, and 10.7 g (0.07 mole) of bromotrimethylsilane is added. The mixture is stirred at 20°–30° for 2–3 days, and to it is then added 20 ml water. The mixture is stirred for about 30 minutes, and the layers are separated. The water layer is extracted several times with $CHCl_3$ (extracts are discarded) and is evaporated to dryness under vacuum. The residue is triturated with acetone to give a solid, which is collected by filtration and recrystallized from water/acetone to afford 2-(1-imidazolyl)-1-phosphonoethanesulfonic acid.

EXAMPLE 2

Synthesis of 1-Phosphono-2-(3-pyridylamino)ethanesulfonic Acid

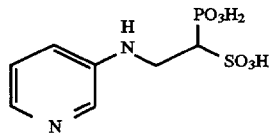

This compound is synthesized in the manner of Example 1, starting with 3-aminopyridine.

EXAMPLE 3

Synthesis of 1-Phosphono-2-(3-piperidinylamino) ethanesulfonic Acid

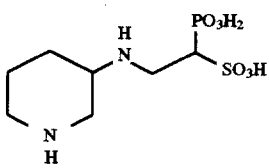

A mixture of 1 g of 1-phosphono-2-(3-pyridinylamino) ethanesulfonic acid and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 1-phosphono-2-(3-piperidinylamino)ethanesulfonic acid.

EXAMPLE 4

Synthesis of 1-Phosphono-2-(2-pyridinylamino) ethanesulfonic Acid

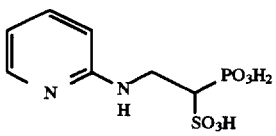

This compound is synthesized in the manner of Example 1, starting with 2-aminopyridine.

EXAMPLE 5

Synthesis of 1-Phosphono-2-((2-piperidinylidene)amino) ethanesulfonic Acid

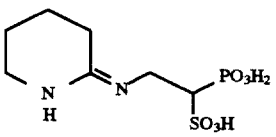

This compound is synthesized by the procedure of Example 3, starting with 1-phosphono-2-(2-pyridinylamino) ethanesulfonic acid.

EXAMPLE 6

Synthesis of 1-Phosphono-2-(2-pyrimidinylamino) ethanesulfonic Acid

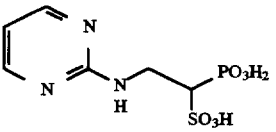

This compound is synthesized in the manner of Example 1, starting with 2-aminopyrimidine.

EXAMPLE 7

Synthesis of 1-Phosphono-2-((1,3-diazacyclohexane-2-ylidene) amino)ethanesulfonic Acid

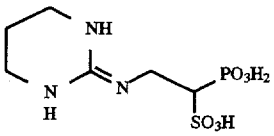

This compound is synthesized by the procedure of Example 3, starting with 1-phosphono-2-(2-pyrimidinylamino)ethanesulfonic acid.

EXAMPLE 8

Synthesis of 1-Phosphono-2-(N-methyl(2-pyridinyl)amino) ethanesulfonic Acid

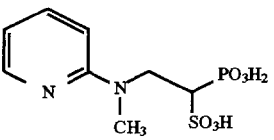

This compound is synthesized in the manner of Example 1, starting with 2-methylaminopyridine.

EXAMPLE 9

Synthesis of 2-[(N-methyl)(3,4,5,6-tetrahydropyridin-2-yl) amino]-1-phosphonoethanesulfonic Acid

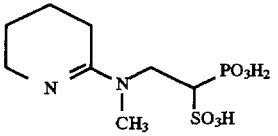

This compound is synthesized by the procedure of Example 3, starting with 2-[N-methyl(2-pyridinyl)amino]-1-phosphonoethanesulfonic acid.

EXAMPLE 10

Synthesis of 1-Phosphono-2-(1-pyrrolidinyl)ethanesulfonic Acid

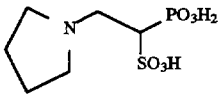

This compound is synthesized by the method of Example 1, starting with pyrrolidine.

EXAMPLE 11

Synthesis of 2-Hexahydro-1H-azepin-1-yl)-1-(phosphono) ethanesulfonic Acid

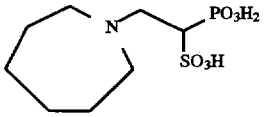

This compound is synthesized by the method of Example 1, starting with hexamethyleneimine.

EXAMPLE 12
Synthesis of 2-(Cyclohexylamino)-1-phosphonoethanesulfonic Acid

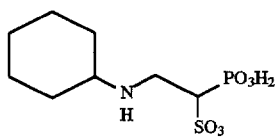

This compound is synthesized by the method of Example 1, starting with cyclohexylamine.

EXAMPLE 13
Synthesis of 2-[2-(Dimethylamino)ethylamino]-1-phosphonoethanesulfonic Acid

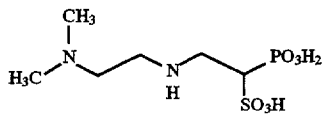

This compound is synthesized by the method of Example 1, starting with N,N-dimethylethylenediamine.

EXAMPLE 14
Synthesis of 2-[2-(Dimethylamino)ethylthio]-1-phosphonoethanesulfonic Acid

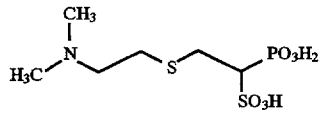

This compound is synthesized by the method of Example 1, starting with 2-dimethylaminoethanethiol.

EXAMPLE 15
Synthesis of 3-Amino-1-phosphonopropanesulfonic Acid

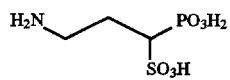

I. Synthesis of Methyl 2-Cyano-1-(dimethoxyphosphinyl)ethanesulfonate

To a solution of 2.3 g (0.01 mole) of methyl 1-dimethoxyphosphinylethylenesulfonate in a mixture of 20 ml ethanol and 10 ml water is added 0.60 g (0.01 mole) of acetic acid followed by 1.3 g (0.02 mole) of potassium cyanide. The mixture is stirred at room temperature for 1–5 hours, 20 ml more water is added, and the mixture is concentrated under vacuum on a rotary evaporator to get rid of the ethanol. The reaction is extracted several times with chloroform. The combined extracts are dried (MgSO$_4$) and the solvent is removed. The resulting oily residue is purified by flash chromatography on silica gel.

II. Synthesis of 2-Cyano-1-phosphonoethanesulfonate

A solution of 2.57 g (0.01 mole) of methyl 2-cyano-1-(dimethoxyphosphinyl)ethanesulfonate in 30 ml chloroform is treated with 10.7 g (0.07 mole) of bromotrimethylsilane. The solution is stirred at room temperature for 2–3 days. Water (20 ml) is added, and the mixture is vigorously stirred for 30 minutes. The solvents are removed under vacuum on a rotary evaporator, and the residue is triturated with acetone to afford 2-cyano-1-phosphonoethanesulfonate.

III. Synthesis of 3-Amino-1-phosphonopropanesulfonic Acid

The hydrogenation of 2-cyano-1-phosphonoethanesulfonate is carried out using the hydrogenation technique of Freifelder (J. Am. Chem. Soc., 82, 2386 (1960)). The cyano compound (2.15 g; 0.01 mole) is placed in 20 ml of 10% methanolic ammonia. Rhodium on alumina (5%) catalyst (0.5 g) is added, and the mixture is hydrogenated at 40 PSI on a Parr apparatus for several hours (until uptake of hydrogen is complete). The catalyst is filtered off, and the filtrate is evaporated dry. The product is purified by dissolving the residue in water, adding ethanol to give a precipitate, and collecting the solids by filtration. Further purification is accomplished by again recrystallizing from water/ethanol.

EXAMPLE 16
Synthesis of 1-Phosphono-2-(3-pyridyl)ethanesulfonic Acid

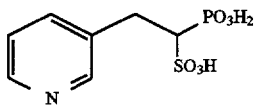

I. Synthesis of 1-Diethoxyphosphinyl-2-(3-pyridyl)ethanesulfonic Acid Lithium Salt A suspension of 2.38 g (0.1 mole) of diethoxyphosphinylmethanesulfonate lithium salt (Carretero, et al.; Tetrahedron, 43, 5125 (1987)) in 50 ml of anhydrous tetrahydrofuran is stirred in a −40° bath under a dry nitrogen atmosphere. To this is added n-butyl lithium (4.4 ml of 2.5M solution in hexanes; 0.011 mole) via syringe over 5 minutes. The reaction mixture is allowed to warm to −15°, and is stirred at this temperature for about one hour. It is then cooled to −78°, and to it is added dropwise over about 5 minutes a solution of 1.27 g (0.1 mole) of 3-(chloromethyl)pyridine in 3 ml of anhydrous THF. (3-(chloromethyl)pyridine is prepared by dissolving a few grams of 3-picolylchloride hydrochloride in a minimum quantity of water and carefully adding excess solid K$_2$CO$_3$ until foaming stops and the water has been absorbed by the K$_2$CO$_3$ leaving the 3-picolylchloride floating on the surface as an oil. This is extracted with a few ml of methylene chloride. The solution is dried with MgSO$_4$ and is evaporated to dryness under vacuum to give 3-(chloromethyl)pyridine. This must be prepared fresh for each use, and heat should be avoided to minimize decomposition. (3-(chloromethyl)pyridine is a severe irritant, and care must be taken in handling it.) The reaction mixture is stirred for 1 hour at −78°, and is then allowed to warm to room temperature over several hours as the bath warms up. It is stirred at ambient temperature for several hours, and is then quenched by addition of 1.2 g (0.02 mole) of acetic acid. The reaction mixture is evaporated to dryness on a rotary evaporator, and the resulting residue is purified by flash chromatography on silica gel using chloroform/methanol as eluant to give 1-diethoxyphosphinyl-2-(3-pyridyl)ethanesulfonic acid lithium salt.

II. Synthesis of 1-Phosphono-2-(3-pyridyl)ethanesulfonic Acid

The above diester is hydrolyzed by dissolving it (2 g) in 20 ml of 6N HCl and heating this solution at reflux for 12–24 hours. It is then evaporated to dryness under vacuum. The residue is dissolved in water and is treated with cation exchange resin in H$^+$ form to remove Li salts. The solution is taken to dryness on a rotary evaporator, and the residue is triturated with acetone. The resulting solid is filtered off and recrystallized from water/ethanol to field 1-phosphono-2-(3-pyridyl)ethanesulfonic acid.

EXAMPLE 17
Synthesis of 1-Methyl-3-(2-phosphono-2-sulfonoethyl) pyridinium Iodide

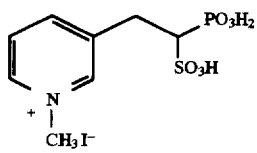

A solution of 2.67 g (0.01 mole) of 1-phosphono-2-(3-pyridinyl)ethanesulfonic acid (prepared as described in Example 16) in 20 ml water and 30 ml ethanol is adjusted to pH 7.0 by addition of 1N aqueous NaOH. To this is added 7.1 g (0.05 mole) of methyl iodide, and the reaction is stirred at 30°–50° for one day. The reaction is evaporated to dryness under reduced pressure. The resulting residue is dissolved in distilled water, and is treated with cation exchange resin in $H^+$ form. The resin is filtered off and the aqueous solution is evaporated to dryness under vacuum. The residue is triturated with acetone to give a solid which is collected by filtration. This is purified by recrystallization from water/acetone to give N-methyl-3-(2-phosphono-2-sulfonoethyl) pyridinium iodide.

EXAMPLE 18
Synthesis of N-Ethyl-3-(2-phosphono-2-sulfonoethyl) pyridinium Iodide

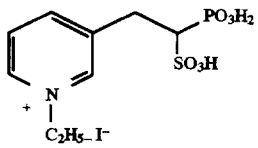

A solution of 2.67 g (0.01 mole) of 1-phosphono-2-(3-pyridyl)ethanesulfonic acid (prepared as described in Example 16) in 20 ml water and 40 ml ethanol is adjusted to pH 7.0 by addition of 1N aqueous NaOH. To this is added 6.24 g (0.04 mole) of ethyl iodide, and the reaction is stirred at 30°–50° for one day. The reaction is evaporated to dryness under reduced pressure. The resulting residue is dissolved in distilled water, and is treated with cation exchange resin in $H^+$ form. The resin is filtered off, the aqueous solution is concentrated to a few ml, and acetone is added dropwise to precipitate the product. This is purified by recrystallization from water/acetone to give N-ethyl-3-(2-phosphono-2-sulfonoethyl)pyridinium iodide.

EXAMPLE 19
Synthesis of N-(2-(Acetylthio)ethyl)-3-(2-phosphono-2-sulfonoethyl)pyridinium Bromide

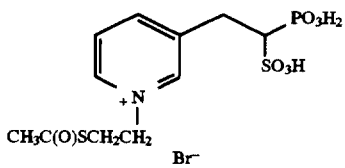

A solution of 2.67 g (0.01 mole) of 1-phosphono-2-(3-pyridyl)ethanesulfonic acid (prepared as described in Example 16) in 20 ml water and 40 ml ethanol is adjusted to pH 7.0 by addition of 1N aqueous NaOH. To this is added 9.16 g (0.05 mole) of S-acetyl-2-bromoethanethiol, and the reaction is heated at 40°–80° for several hours. The reaction is evaporated to dryness under reduced pressure. The resulting residue is triturated with acetone several times (acetone extracts are discarded). The remaining solid is dissolved in distilled water, and is treated with cation exchange resin in $H^+$ form. The resin is filtered off, the aqueous solution is concentrated to a few ml, and acetone is added dropwise to precipitate the product. This is purified by recrystallization from water/acetone to give N-(2-(acetylthio)ethyl)-3-(2-phosphono-2-sulfonoethyl)pyridinium bromide.

EXAMPLE 20
Synthesis of 3-(2-Phosphono-2-sulfonoethyl)-N-(2-thioethyl)pyridinium Chloride

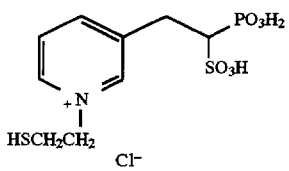

A solution of 1 g of N-(2-(acetylthio)ethyl)-3-(2-phosphono-2-sulfonoethyl)pyridinium bromide in 50 ml of water is treated with anion exchange resin in chloride form. The solution is concentrated to 20 ml, and 20 ml of 12N HCl is added. The solution is heated at reflux under a nitrogen atmosphere for 12 hours, and is then evaporated dry. The residue is dissolved in 50 ml of fresh 6N HCl and is again evaporated to dryness. It is then taken up in a few ml of water and is reprecipitated with ethanol to yield 3-(2-phosphono-2-sulfonoethyl)-N-(2-thioethyl)pyridinium chloride. All of these operations are carried out under $N_2$ atmosphere using deoxygenated solvents to minimize disulfide formation.

EXAMPLE 21
Synthesis of 1-Phosphono-2-(2-pyridyl)ethanesulfonic Acid

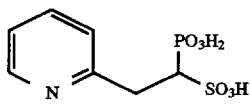

This compound is synthesized according to the method in Example 16, starting with 2-picolyl chloride hydrochloride.

EXAMPLE 22
Synthesis of N-Methyl-2-(2-phosphono-2-sulfonoethyl) pyridinium Iodide

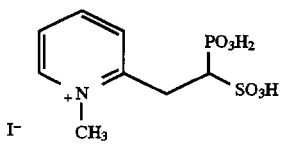

This compound is synthesized by the method of Example 17, starting with 1-phosphono-2-(2-pyridyl)ethanesulfonic acid.

EXAMPLE 23

Synthesis of N-Ethyl-2-(2-phosphono-2-sulfonoethyl) pyridinium Iodide

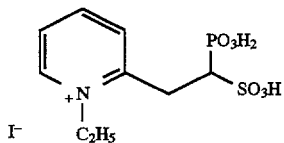

This compound is synthesized by the method of Example 18, starting with 1-phosphono-2-(2-pyridyl)ethanesulfonic acid.

EXAMPLE 24

Synthesis of N-(2-(Acetylthio)ethyl)-2-(2-phosphono-2-sulfonoethyl)pyridinium Bromide

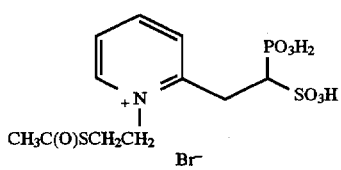

This compound is synthesized by the method of Example 19 starting with 1-phosphono-2-(2-pyridyl)ethanesulfonic acid.

EXAMPLE 25

Synthesis of 2-(2-Phosphono-2-sulfonoethyl)-N-(2-thioethyl)pyridinium Chloride

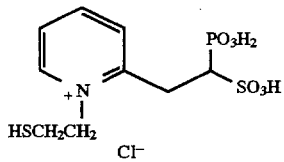

This compound is synthesized by the method of Example 20 starting with N-(2-(acetylthio)ethyl)-2-(2-phosphono-2-sulfonoethyl)pyridinium bromide.

EXAMPLE 26

Synthesis of 2-(1-Methyl-2-piperidinyl)-1-phosphonoethanesulfonic Acid

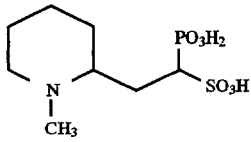

A mixture of 1 g of N-methyl-2-(2-phosphono-2-sulfonoethyl)pyridinium iodide and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 2-(1-methyl-2-piperidinyl)-1-phosphonoethanesulfonic acid.

EXAMPLE 27

Synthesis of N,N-Dimethyl-2-(2-phosphono-2-sulfonoethyl)piperidinium Iodide

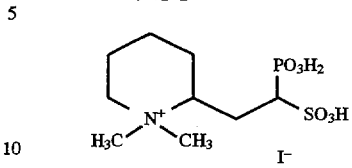

This is prepared by the method used in Example 17, starting with 2-(1-methyl-2-piperidinyl)-1-phosphonoethanesulfonic acid.

EXAMPLE 28

Synthesis of N-Methyl-N-ethyl-2-(2-phosphono-2-sulfonoethyl)piperidinium Iodide

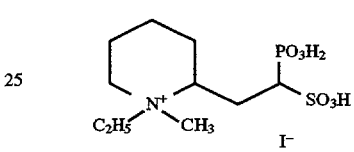

This is prepared by the method used in Example 18, starting with 2-(1-methyl-2-piperidinyl)-1-phosphonoethanesulfonic acid.

EXAMPLE 29

Synthesis of N-(2-(Acetylthio)ethyl)-N-methyl-2-(2-phosphono-2-sulfonoethyl)piperidinium Bromide

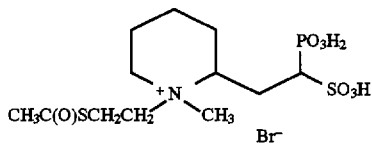

This is prepared by the method used in Example 19, starting with 2-(1-methyl-2-piperidinyl)-1-phosphonoethanesulfonic acid.

EXAMPLE 30

Synthesis of N-Methyl-N-(2-thioethyl)-2-(2-phosphono-2-sulfonoethyl)piperidinium Chloride

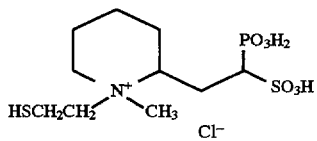

This is prepared by the method used in Example 20, starting with N-(2-(acetylthio)ethyl)-N-methyl-2-(2-phosphono-2-sulfonoethyl)piperidinium bromide.

EXAMPLE 31

Synthesis of 2-(2-Piperidinyl)-1-phosphonoethanesulfonic Acid

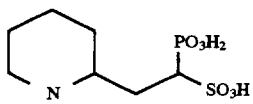

A mixture of 1 g of 1-phosphono-2-(2-pyridinyl) ethanesulfonic acid and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 1-phosphono-2-(2-piperidinyl)ethanesulfonic acid.

EXAMPLE 32

Synthesis of 2-(3-Piperidinyl)-1-phosphonoethanesulfonic Acid

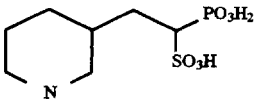

This compound is prepared by the method of Example 31 starting with 1-phosphono-2-(3-pyridinyl)ethanesulfonic acid.

EXAMPLE 33

Synthesis of 2-(1-Methyl-3-piperidinyl)-1-phosphonoethanesulfonic Acid

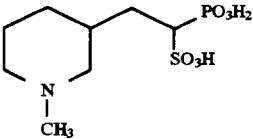

This compound is prepared by the method of Example 26, starting with 1-methyl-3-(2-phosphono-2-sulfonoethyl) pyridinium iodide.

EXAMPLE 34

Synthesis of N,N-Dimethyl-3-(2-phosphono-2-sulfonoethyl)piperidinium Iodide

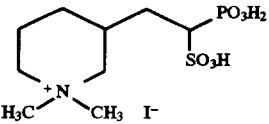

This is prepared by the method used in Example 17, starting with 2-(1-methyl-3-piperidinyl)-1-phosphonoethanesulfonic acid.

EXAMPLE 35

Synthesis of N-(2-(Acetylthio)ethyl)-N-methyl-3-(2-phosphono-2-sulfonoethyl)piperidinium Bromide

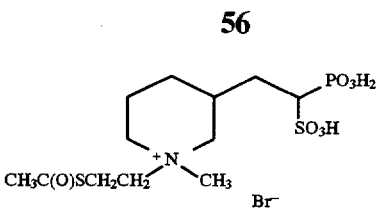

This is prepared by the method used in Example 19, starting with 2-(1-methyl-3-piperidinyl)-1-phosphonoethanesulfonic acid.

EXAMPLE 36

Synthesis of N-Methyl-N-(2-thioethyl)-3-(2-phosphono-2-sulfonoethyl)piperidinium Chloride

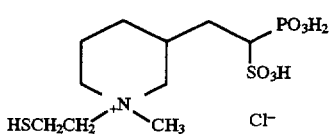

This is prepared by the method used in Example 20, starting with N-(2-(acetylthio)ethyl)-N-methyl-3-(2-phosphono-2-sulfonoethyl)piperidinium bromide.

EXAMPLE 37

Synthesis of Phosphono(2-pyridinylthio)methanesulfonic acid

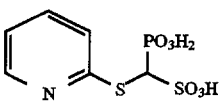

A suspension of 2.38 g (0.01 mole) of diethoxyphosphinylmethanesulfonate lithium salt (Carretero, et al.; Tetrahedron, 43, 5125 (1987)) in 50 ml of anhydrous tetrahydrofuran is stirred in a −40° bath under a dry nitrogen atmosphere. To this is added n-butyl lithium (4.4 ml of 2.5M solution in hexanes; 0.011 mole) via syringe over 5 minutes. The reaction mixture is allowed to warm to −15°, and is stirred at this temperature for about one hour. To it is then added rapidly a solution of 2.2 g (0.01 mole) of 2,2'-dipyridyl disulfide in 30 ml of anhydrous THF. The reaction mixture is stirred for 1 hour at −15°, and is then allowed to warm to room temperature over several hours as the bath warms up. It is stirred at ambient temperature for several hours, and is then quenched by addition of 50 ml of water. The reaction mixture is concentrated under vacuum on a rotary evaporator to get rid of the THF, and the aqueous layer is extracted with ether to remove some impurities. The water layer is concentrated to 10 ml on a rotary evaporator, and 10 ml of 12N HCl is added. The solution is heated at reflux for 12–24 hours, and is evaporated to dryness under vacuum. The residue is dissolved in water and is treated with cation exchange resin in H⁺ form to remove Li salts. The solution is taken to dryness on a rotary evaporator, and the residue is triturated with acetone. The resulting solid is filtered off and recrystallized from water/ethanol to yield phosphono(2-pyridinylthio)methanesulfonic acid.

EXAMPLE 38

Synthesis of 4-Amino-1-phosphonobutanesulfonic Acid

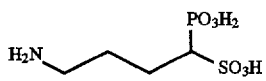

I. Synthesis of 3-Cyano-1-diethoxyphosphinylpropanesulfonic Acid Lithium Salt

A suspension of 2.38 g (0.01 mole) of diethoxyphosphinylmethanesulfonate lithium salt (Carretero, et al.; Tetrahedron, 43, 5125 (1987)) in 50 ml of anhydrous tetrahydrofuran is stirred in a −40° bath under a dry nitrogen atmosphere. To this is added n-butyl lithium (4.4 ml of 2.5M solution in hexanes; 0.011 mole) via syringe over 5 minutes. The reaction mixture is allowed to warm to −15° and is stirred at this temperature for about one hour. To it is then added rapidly a solution of 0.53 g (0.01 mole) of acrylonitrile in 3 ml of anhydrous THF. The reaction mixture is stirred for 1 hour at −15°, and is then allowed to warm to room temperature over several hours as the bath warms up. It is stirred at ambient temperature for several hours, and then is quenched by addition of 50 ml of water containing 0.6 g (0.01 mole) of acetic acid. The reaction mixture is concentrated under vacuum on a rotary evaporator to get rid of the THF, and the aqueous layer is extracted with ether to remove some impurities. The water layer is evaporated to dryness under vacuum, and the resulting residue is purified by flash chromatography on silica gel using chloroform/methanol as eluant, to afford 3-cyano-1-diethoxyphosphinylpropanesulfonic acid lithium salt.

II. Synthesis of 4-Amino-1-phosphonobutanesulfonic Acid

The hydrogenation of 3-cyano-1-diethoxyphosphinylpropanesulfonic acid lithium salt is carried out using the hydrogenation technique of Freifelder (J. Am. Chem. Soc., 82, 2386 (1960)). The cyano compound (2.62 g; 0.01 mole) is placed in 20 ml of 10% methanolic ammonia. Rhodium on alumina (5%) catalyst (0.5 g) is added, and the mixture is hydrogenated at 40 PSI on a Parr apparatus for several hours (until uptake of hydrogen is complete). The catalyst is filtered off, and the filtrate is evaporated dry. The product is hydrolyzed by dissolving the residue in 25 ml of 6N HCl and refluxing the solution for 12-24 hours. It is then evaporated to dryness under vacuum on a rotary evaporator. Distilled water (25 ml) is added, and the solution is again evaporated dry. The resulting residue is dissolved in a few ml H$_2$O, and ethanol is added to precipitate a solid. This is recrystallized from water/ethanol to yield 4-amino-1-phosphonobutanesulfonic acid.

EXAMPLE 39

Synthesis of 1-Hydroxy-1-phosphono-2-(3-pyridinyl)ethanesulfonic Acid

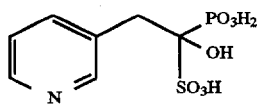

I. Synthesis of 1-Diethoxyphosphinyl-1-hydroxy-2-(3-pyridinyl)ethanesulfonic Acid Lithium Salt A suspension of 3.29 g (0.01 mole) of 1-diethoxyphosphinyl-2-(3-pyridinyl)ethanesulfonic acid lithium salt (from part I of Example 16) in 50 ml of anhydrous tetrahydrofuran is stirred in a −40° bath under a dry nitrogen atmosphere. To this is added n-butyl lithium (4.4 ml of 2.5M solution in hexanes; 0.011 mole) via syringe over 5 minutes. The reaction mixture is allowed to warm to −15°, and is stirred at this temperature for about one hour. It is then cooled to −78°, and to it is added dropwise a solution of 3.44 g (0.015 mole) of camphorylsulfonyloxaziridine (J. Am. Chem. Soc., 112, 6679(1990)) in 50 ml of anhydrous THF. The reaction mixture is stirred for a few minutes at −78°, and then is placed in an ice/water bath. It is stirred at 0° for 2–10 minutes, and then is again cooled to −78°. The reaction mixture is quenched by addition of 1.2 g (0.02 mole) of acetic acid and the solvents are removed under vacuum on a rotary evaporator. The residue was purified by chromatography on silica gel using chloroform/methanol as eluant, to yield 1-diethoxyphosphinyl-1-hydroxy-2-(3-pyridinyl)ethanesulfonic acid lithium salt.

II. Synthesis of 1-Hydroxy-1-phosphono-2-(3-pyridinyl)ethanesulfonic Acid

Hydrolysis of the above diester is effected by dissolving it (1 g) in 15 ml of 6N HCl and heating the solution at reflux for 12–24 hours. The solution is then evaporated to dryness. The residue is redissolved in water and treated with cation exchange resin in H+ form. The solution is again taken to dryness and is triturated with acetone to give a solid. This is recrystallized from water/ethanol to yield 1-hydroxy-1-phosphono-2-(3-pyridinyl)ethanesulfonic acid.

EXAMPLE 40

Synthesis of 1-Methyl-3-(2-hydroxy-2-phosphono-2-sulfonoethyl)pyridinium Iodide

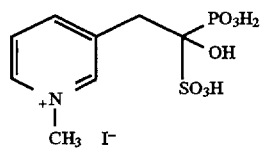

This compound is synthesized by the method of Example 17, starting with 1-hydroxy-1-phosphono-2-(3-pyridinyl)ethanesulfonic acid.

EXAMPLE 41

Synthesis of N-Ethyl-3(2-hydroxy-2-phosphono-2-sulfonoethyl)pyridinium Iodide

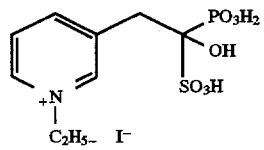

This compound is synthesized by the method of Example 18, starting with 1-hydroxy-1-phosphono-2-(3-pyridinyl)ethanesulfonic acid.

EXAMPLE 42

Synthesis of N-(2-(Acetylthio)ethyl)-3-(2-hydroxy-2-phosphono-2-sulfonoethyl)pyridinium Bromide

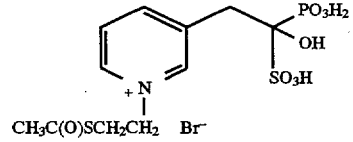

This compound is synthesized by the method of Example 19, starting with 1-hydroxy-1-phosphono-2-(3-pyridinyl)ethanesulfonic acid.

EXAMPLE 43

Synthesis of 3-(2-Hydroxy-2-phosphono-2-sulfonoethyl)-N-(2-thioethyl)pyridinium Chloride

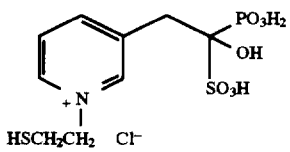

This compound is synthesized by the method of Example 20, starting with N-(2-(acetylthio)ethyl)-3-(2-hydroxy-2-phosphono-2-sulfonoethyl)pyridinium bromide.

EXAMPLE 44

Synthesis of 1-Hydroxy-1-phosphono-2-(2-pyridyl) ethanesulfonic Acid

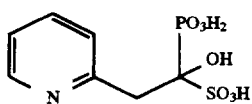

This compound is synthesized according to the method in Example 39, starting with 1-diethoxyphosphinyl-2-(2-pyridinyl)ethanesulfonic acid lithium salt.

EXAMPLE 45

Synthesis of N-Methyl-2-(2-hydroxy-2-phosphono-2-sulfonoethyl)pyridinium Iodide

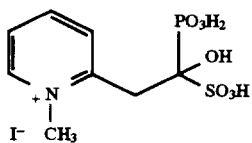

This compound is synthesized by the method of Example 17, starting with 1-hydroxy-1-phosphono-2-(2-pyridinyl) ethanesulfonic acid.

EXAMPLE 46

Synthesis of N-Ethyl-2-(2-hydroxy-2-phosphono-2-sulfonoethyl)pyridinium Iodide

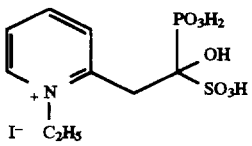

This compound is synthesized by the method of Example 18, starting with 1-hydroxy-1-phosphono-2-(2-pyridinyl) ethanesulfonic acid.

EXAMPLE 47

Synthesis of N-(2-(Acetylthio)ethyl)-2-(2-hydroxy-2-phosphono-2-sulfonoethyl)pyridinium Bromide

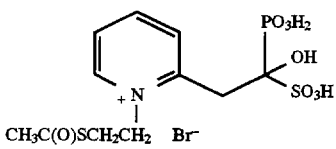

This compound is synthesized by the method of Example 19 starting with 1-hydroxy-1-phosphono-2-(2-pyridinyl) ethanesulfonic acid.

EXAMPLE 48

Synthesis of 2-(2-Hydroxy-2-phosphono-2-sulfonoethyl)-N-(2-thioethyl)pyridinium Chloride

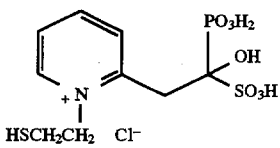

This compound is synthesized by the method of Example 20 starting with N-(2-(acetylthio)ethyl)-2-(2-hydroxy-2-phosphono-2-sulfonoethyl)pyridinium bromide.

EXAMPLE 49

Synthesis of 1-Hydroxy-2-(1-methyl-2-piperidinyl)-1-phosphonoethanesulfonic Acid

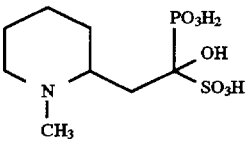

A mixture of 1 g of N-methyl-2-(2-hydroxy-2-phosphono-2-sulfonoethyl)pyridinium iodide and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 1-hydroxy-2-(1-methyl-2-piperidinyl)-1-phosphonoethanesulfonic acid.

EXAMPLE 50

Synthesis of N,N-Dimethyl-2-(2-hydroxy-2-phosphono-2-sulfonoethyl)piperidinium Iodide

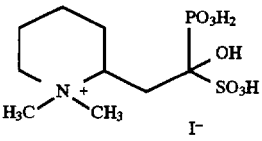

This is prepared by the method used in Example 17, starting with 1-hydroxy-2-(1-methyl-2-piperidinyl)-1-phosphonoethanesulfonic acid.

EXAMPLE 51

Synthesis of N-Methyl-N-ethyl-2-(2-hydroxy-2-phosphono-2-sulfonoethyl)piperidinium Iodide

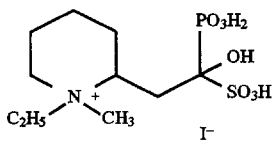

This is prepared by the method used in Example 18, starting with 1-hydroxy-2-(1-methyl-2-piperidinyl)-1-phosphonoethanesulfonic acid.

EXAMPLE 52
Synthesis of N-(2-(Acetylthio)ethyl)-N-methyl-2-(2-hydroxy-2-phosphono-2-sulfonoethyl)piperidinium Bromide

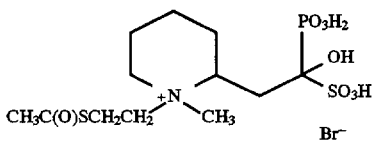

This is prepared by the method used in Example 19, starting with 1-hydroxy-2-(1-methyl-2-piperidinyl)-1-phosphonoethanesulfonic acid.

EXAMPLE 53
Synthesis of N-Methyl-N-(2-thioethyl)-2-(2-hydroxy-2-phosphono-2-sulfonoethyl)piperidinium Chloride

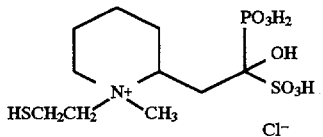

This is prepared by the method used in Example 20, starting with N-(2-(acetylthio)ethyl)-N-methyl-2-(2-hydroxy-2-phosphono-2-sulfonoethyl)piperidinium bromide.

EXAMPLE 54
Synthesis of 1-Hydroxy-2-(2-Piperidinyl)-1-phosphonoethanesulfonic Acid

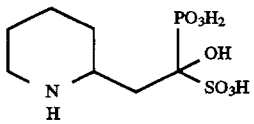

A mixture of 1 g of 1-hydroxy-1-phosphono-2-(2-pyridinyl)ethanesulfonic acid and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 1-hydroxy-1-phosphono-2-(3-piperidinyl)ethanesulfonic acid.

EXAMPLE 55
Synthesis of 1-Hydroxy-2-(3-piperidinyl)-1-phosphonoethanesulfonic Acid

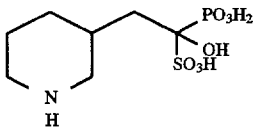

This compound is prepared by the method of Example 54 starting with 1-hydroxy-1-phosphono-2-(3-pyridinyl) ethanesulfonic acid.

EXAMPLE 56
Synthesis of 1-Hydroxy-2-(1-methyl-3-piperidinyl)-1-phosphonoethanesulfonic Acid

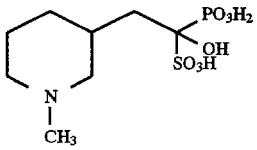

This compound is prepared by the method of Example 54, starting with 1-methyl-3-(2-hydroxy-2-phosphono-2-sulfonoethyl)pyridinium iodide.

EXAMPLE 57
Synthesis of N,N-Dimethyl-3-(2-hydroxy-2-phosphono-2-sulfonoethyl)piperidinium Iodide

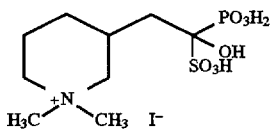

This is prepared by the method used in Example 17, starting with 1-hydroxy-2-(1-methyl-3-piperidinyl)-1-phosphonoethanesulfonic acid.

EXAMPLE 58
Synthesis of N-(2-(Acetylthio)ethyl)-N-methyl-3-(2-hydroxy-2-phosphono-2-sulfonoethyl)piperidinium Bromide

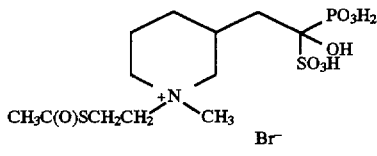

This is prepared by the method used in Example 19, starting with 1-hydroxy-2-(1-methyl-3-piperidinyl)-1-phosphonoethanesulfonic acid.

EXAMPLE 59
Synthesis of N-Methyl-N-(2-thioethyl)-3-(2-hydroxy-2-phosphono-2-sulfonoethyl)piperidinium Chloride

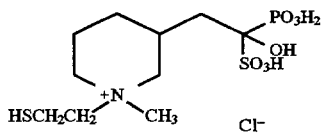

This is prepared by the method used in Example 20, starting with N-(2-(acetylthio)ethyl)-N-methyl-3-(2-hydroxy-2-phosphono-2-sulfonoethyl)piperidinium bromide.

EXAMPLE 60

Synthesis of Dihydro-6-phosphono-1-pyrindine-6-sulfonic Acid

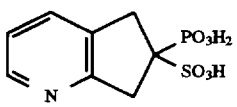

To 70 ml of anhydrous dimethylsulfoxide (DMSO), stirred under nitrogen atmosphere in an ice bath, is added 1.6 g of 60% NaH in mineral oil (0.04 mole). When this is dissolved, there is added dropwise to the solution (still stirred at 0°) a solution of diethoxyphosphinyl-methanesulfonic acid lithium salt (4.76 g, 0.02 mole) in 30 ml of DMSO. The reaction mixture is stirred at room temperature for one hour. To it is then added dropwise a solution of 3.48 g (0.02 mole) of 2,3-bis(chloromethyl) pyridine (see K. Tsuda, et al., Chem. Pharm. Bull., 1, 142 (1953)) in 15 mi of DMSO. The mixture is stirred at room at 80° for 1–3 hours. The DMSO is removed under vacuum, and the residue is purified by flash chromatography on silica gel using 1–15% methanol in methylene chloride gradient as eluant.

The above ester is hydrolyzed by refluxing it in 6N HCl for 20 hours. Upon concentration of the reaction solution and cooling it in ice a precipitate forms. This is recrystallized from water to afford dihydro-1-pyrindine-6-phosphono-6-sulfonic acid.

EXAMPLE 61

Synthesis of Octahydro-6-phosphono-1-pyrindine-6-carboxylic Acid

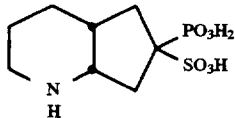

1.0 g of dihydro-6-phosphono-1-pyrindine-6-carboxylic acid hydrochloride (from example 60) in 50 ml of $H_2O$ with 0.5 g of $PtO_2$ is hydrogenated on a Parr apparatus at 40 PSI for 3 days. The catalyst is filtered off, and the filtrate is taken to dryness under vacuum. The resulting solid is taken up in the minimum amount of water, and precipitated by slow addition of ethanol to give octahydro-6-phosphono-1-pyrindine-6-sulfonic acid.

EXAMPLE 62

Capsules are prepared having the following composition:

| Active Ingredient | Mg Per Capsule |
| --- | --- |
| 1-hydroxy-1-phosphono-2-(3-pyridinyl)ethanesulfonic Acid | 350.0 |
| Excipients | |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

Any of the compounds prepared according to Examples 1 to 61 may be substituted for the active ingredient in the capsule prepared hereinabove.

EXAMPLE 63

Tablets are prepared having the following composition:

| Active Ingredient | Mg Per Tablet |
| --- | --- |
| 3-(2-Hydroxy-2-phosphono-2-sulfonoethyl)-N-(2-thioethyl)pyridinium chloride | 700.00 |
| Excipients | |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

Any of the compounds prepared according to Examples 1 to 61 may be substituted for the active ingredient in the tablet prepared hereinabove.

EXAMPLE 64

Injectable solutions are prepared by conventional methods using 100 ml of physiological saline solution and 70 mg P of 3-(2-hydroxy-2-phosphono-2-sulfonoethyl)-N-(2-thioethyl)pyridinium chloride, adjusted to pH=7.4.

One injection, one time daily for 4 days, results in appreciable alleviation of hypercalcemia of malignancy in patients weighing approximately 70 kilograms.

Any of the compounds prepared according to Examples 1 to 61 may be substituted for the active ingredient in the injection prepared hereinabove.

EXAMPLE 65

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which is subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example 63 twice daily two hours before or after meals for a period of three months. His clinical symptoms of pain and swelling, particularly with extended walking, improves significantly after his 3 months of therapy. At the confusion of three months at a dosage of 2 tablets per day, the therapy is continued at one-half the dosage originally prescribed (i.e. 1 tablets per day) indefinitely.

EXAMPLE 66

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the tablets prepared in Example 63, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE 67

A female of Hispanic origin, twelve years of age, weighing approximately 37 kilograms, presents to the physician with idiopathic juvenile rheumatoid arthritis. Her symptoms include marked intimation of multiple joints, complicated by heat and tenderness and indicating rapid and pathological degeneration of joint function.

Her physician refers her to a rheumatologist who immediately prescribes aggressive therapy by IV administration of the solution prepared as described in Example 64 over a period of three days, at the rate of 1 injection per day, administered over two hours. At the conclusion of the IV regimen, the physician prescribes the tablets prepared as described in Example 63, for a period of two months, during which she exhibits marked improvement with increased mobility and decreased pain. For the succeeding two months, the physician reduces her dose to ¾ of the original oral dose by prescribing 3 tablets over a period of two days, i.e. one 2-tablet day alternating with one 1-tablet day. At the conclusion of this regimen the dosage is again reduced to ¼ of the original dose by giving her the tablets prepared as described in Example 63, 1 tablet every day for an additional four months.

EXAMPLE 68

A 60-year-old Caucasian female weighing 62 kg, experiences severe back pain. Her physician, with the aid of a radiologist diagnoses her as having a crush fracture of the L1 vertebrae presumably due to osteoporotic bone loss. The patient is prescribed a three month, once-daily dosage regimen of a 700 mg tablet prepared according to the procedure described in Example 62. The 700 mg tablet is taken either two hours before or two hours after any given meal. After three months, the dosage is reduced to a 350 mg capsule, prepared as described in Example 63, taken every other day for a period of three months. Her physician then puts her on a maintenance dosing regimen wherein she takes a 100 mg capsule every day for six months. After six months on the maintenance dosing regimen the patient is not experiencing any further back pain. Follow-up x-rays reveal no additional fractures.

EXAMPLE 69

A 75-year-old Oriental female weighing 53 kg suffers a fractured hip after a fall. She is hospitalized and diagnosed as having osteoporosis. A treatment regimen of calcitonin injections is prescribed. The calcitonin injections are painful to the patient and she is unable to comply with the calcitonin regimen. Her physician then switches her therapy to an oral phosphonate regimen. She is administered a 700 mg tablet prepared according to the procedure described in Example 63, twice daily for one month. At the end of this one month of therapy, she is given a 700 mg tablet, once daily for two months. At the end of this two month period, she is given a 100 mg capsule, prepared according to the procedure described in Example 12, daily for three months. A follow-up visit to her physician reveals no apparent decrease in mineral density of the forearm as determined by photonabsorptimetry.

EXAMPLE 70

A 85-year-old Native American male weighing 65 kg presents to his physician with severe back pain. X-rays reveal multiple minor vertebral body collapse resulting from significant bone loss due to osteoporosis. The patient is prescribed a two month regimen of a 700 mg tablet and a 350 mg capsule to be taken on the same day, eight hours apart, prepared according to the procedures described in Examples 63 and 62, respectively. After two months on this regimen, his dosage is reduced to 350 mg tablet once a day for two months. X-rays are taken and an additional crush fracture is noted. He is then put on a maintenance regimen of a 100 mg capsule, prepared according to the procedure described in Example 62, once a day for six months. At the end of this six months, no significant apparent decrease in bone density is observed.

What is claimed is:

1. A phosphonosulfonate, or the pharmaceutically-acceptable salt or ester thereof, according to formula (I):

wherein (A)

(1) A is selected from the group consisting of $SR^1$; $R^2SR^1$; amino; hydroxy;

(2) B is (a) —$NH_2$;

(b) a saturated or unsaturated $C_1$–$C_{15}$ alkyl chain substituted with one or more substituents selected from the group consisting of $R^3N(R^4)_2$; —$R^3[N(R^5)_3]$+; —$R^3N(R^4)C(O)R^4$; —$R^3N(R^4)C(S)R^4$; —$R^3N(R^4)C(N)R^4$; and —$R^3C(O)N(R^4)_2$;

(c) a saturated or unsaturated heteroalkyl chain having from 2 to 15 chain atoms, where one or more of said chain atoms is nitrogen; and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) a saturated or unsaturated heteroalkyl chain having from 2 to 15 chain atoms, where one or more of said chain atoms is selected from S and 0; and where said heteroalkyl chain is substituted with one or more substituents selected from the group consisting of —R³N(R⁴)₂; —R³[—N(R⁵)₃]+; —R³N(R⁴)C(O)R4; —R³N(R⁴)C(S)R⁴; —R³N(R⁴)C(N)R⁴; and —R³C(O)N(R⁴)₂; or (e) R⁶—L— where
  (i) L is selected from the group consisting of covalent bond; N; —N(R⁵)₂⁺; S; O; a saturated or unsaturated C₁–C₁₅ alkyl chain, where said alkyl chain is unsubstituted or is substituted with one or more of alkyl, alkenyl, alkoxy, hydroxy, oxo, thioxo, amine, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and a saturated or unsaturated heteroalkyl chain having from 2 to 15 chain atoms, where one or more of said chain atoms is N, S, or O, and where said heteroalkyl chain is unsubstituted or is substituted with one or more of alkyl, alkenyl, alkoxy, hydroxy, oxo, thioxo, amino, aminoalkyl, cyano, quaternary amine, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and
  (ii) R⁶ is selected from the group consisting of saturated monocyclic or polycyclic carbocyclic rings; unsaturated monocyclic or polycyclic rings; saturated monocyclic or polycyclic heterocyclic rings and unsaturated monocyclic or polycyclic heterocyclic rings wherein R⁶ is unsubstituted or is substituted with one or more substituents independently selected from the group consisting of hydrogen; —R³SR¹; unsubstituted C₁–C₈ alkyl or C₁–C₈ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —R³OR⁴; —R³CO₂R⁴; R³O₂CR⁴; —R³N(R⁴)₂; R³[—N(R⁵)₃]+; —R³N(R⁴)C(O)R⁴; —R³N(R⁴)C(S)R⁴; —R³N(R⁴)C(N)R⁴; —R³C(O)N(R⁴)₂; halogen; —R³C(O)R⁴; arylalkyl; nitro; unsubstituted aryl or aryl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and hydroxy; and (3)
(a) R¹ is independently selected from the group consisting of hydrogen; —C(O)R⁷; C(S)R⁷; —C(O)N(R⁷)₂; —C(O)OR⁷; —C(S)N(R⁷)₂; and —C(S)OR⁷; where R⁷ is hydrogen or unsubstituted C₁–C₈ alkyl or C₁–C₈ alkyl substituted win one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(b) R² is unsubstituted C₁–C₈ alkyl or C₁–C₈ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(c) R³ is selected from the group consisting of covalent bond and unsubstituted C₁–C₈ alkyl or C₁–C₈ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) R⁴ is independently selected from the group consisting of hydrogen; unsubstituted C₁–C₈ alkyl or C₁–C₈ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and —R²SR¹; and (e) R⁵ is independently selected from the group consisting of unsubstituted C₁–C₁₅ alkyl or C₁–C₁₅ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl; or alkynyl; unsubstituted phenyl or phenyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; benzyl; and —R²SR¹;

or

A and B are covalently linked together with C* to form a monocyclic ring of formula (a); or a bicyclic ring of formula (b):

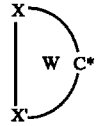

(a)

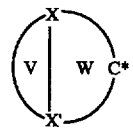

(b)

where
(1) W is a saturated or unsaturated carbocyclic ring formed by C*, X, and X', said carbocyclic ring having a total of from 3 to 6 ring carbon atoms, where said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; or a saturated or unsaturated heterocyclic ring formed by C*, X, and X', said heterocyclic ring having a total of from 4 to 6 ring atoms, where one or more of said ring atoms is N, O, or S, and where said heterocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(2) V is a saturated or unsaturated carbocyclic ring formed by X and X', said carbocyclic ring having a total of from 3 to 8 ring carbon atoms, and where said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; or a saturated or unsaturated heterocyclic ring formed by X and X', said heterocyclic ring having a total of from 3 to 8 ring atoms, where one or more of said ring atoms is N, O, or S, and where said heterocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and (3) X and X' are independently N or C; except that if neither V nor W is a nitrogen containing heterocycle, then at least one of V or W is substituted with one or more substituents selected from the group consisting of —$R^3N(R^4)_2$; $R^3[-N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl; or (C)

(1) A is selected from the group consisting of hydrogen; halogen; $SR^1$; $R^2SR^1$; amino; hydroxy; and unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(2) B is a radical which contains less than 7 carbons wherein B is chosen from;

(a) —$NH_2$;

(b) a saturated or unsaturated $C_1$–$C_6$ alkyl chain substituted with one or more substituents selected from the group consisting of —$R^3N(R^4)_2$; —$R^3N(R^4)C(O)R^4$; —$R^3N(R^4)C(S)R^4$; $R^3N(R^4)C(N)R^4$; and —$R^3C(O)N(R^4)_2$;

(c) a saturated or unsaturated heteroalkyl chain having from 2 to 15 chain atoms, where one or more of said chain atoms is nitrogen; and where said heteroalkyl chain is unsubstituted or is substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) a saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; $R^3N(R^4)C(O)R4$; —$R^3N(R^4)C(S)R^4$; —$R^3N(R^4)C(N)R^4$; and —$R^3C(O)N(R^4)_2$; or (e) $R^6$—L— where (i) L is selected from the group consisting of covalent bond; N; S; O; a saturated or unsaturated $C_1$–$C_5$ alkyl chain, where said alkyl chain is unsubstituted or is substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and a saturated or unsaturated heteroalkyl chain having from 2 to 15 chain atoms, where one or more of said chain atoms is N, S, or O, and where said heteroalkyl chain is unsubstituted or is substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and (ii) $R^6$ is selected from the group consisting of saturated monocyclic rings; unsaturated monocyclic carbocyclic rings; saturated monocyclic or polycyclic heterocyclic rings and unsaturated monocyclic or polycyclic heterocyclic rings wherein $R^6$ is unsubstituted or is substituted with one or more substituents independently selected from the group consisting of hydrogen; —$R^3SR^1$; unsubstituted $C_1$–$C_6$ alkyl or $C_1$–$C_5$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —$R^3OR^4$; $R^3CO_2R^4$; —$R^3O_2CR^4$; —$R^3N(R^4)_2$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; unsubstituted aryl or aryl substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and hydroxy; and (3)
- (a) $R^1$ is independently selected from the group consisting of hydrogen; —C(O)$R^7$; —C(S)$R^7$; —C(O)N($R^7$)$_2$; —C(O)O$R^7$; —C(S)N($R^7$)$_2$; and —C(S)O$R^7$; where $R^7$ is hydrogen or unsubstituted $C_1$–$C_6$ alkyl or $C_1$–$C_6$ alkyl substituted win one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;
- (b) $R^2$ is unsubstituted $C_1$–$C_6$ alkyl or $C_1$–$C_6$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;
- (c) $R^3$ is selected from the group consisting of covalent bond and unsubstituted $C_1$–$C_6$ alkyl or $C_1$–$C_5$ alkyl substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;
- (d) $R^4$ is independently selected from the group consisting of hydrogen; unsubstituted $C_1$–$C_6$ alkyl or $C_1$–$C_5$ alkyl substituted with one or more of alkyl, alkenyl, alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and —$R^2SR^1$; and
- (e) $R^5$ is independently selected from the group consisting of unsubstituted $C_1$–$C_6$ alkyl or $C_1$–$C_5$ alkyl substituted with one or more of alkoxy, hydroxy, oxo, thioxo, amino, aminoalkyl, cyano, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; unsubstituted phenyl or phenyl substituted with one or more of hydroxy, oxo, thioxo, amino, amidinoalkyl, halo, thio; or (D)
- (1) A is selected from the group consisting of hydrogen; halogen; $SR^1$; $R^2SR^1$; amino; hydroxy; and unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;
- (2) B is selected from charged radicals selected from the group consisting of;
  - (b) a saturated or unsaturated $C_1$–$C_{15}$ alkyl chain substituted with one or more substituents selected from the group consisting of —$R^3N(R^4)_2$; —$R^3$[—N($R^5$)$_3$]+; —$R^3N(R^4)C(O)R^4$; —$R^3N(R^4)C(S)R^4$; —$R^3N(R^4)C(N)R^4$; and —$R^3C(O)N(R^4)_2$;
  - (c) a saturated or unsaturated heteroalkyl chain having from 2 to 15 chain atoms, where one or more of said chain atoms is nitrogen; and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; wherein the chain with its substituents, if any, must be charged;
  - (d) a saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3$[—N($R^5$)$_3$]+; —$R^3N(R^4)C(O)R^4$; —$R^3N(R^4)C(S)R^4$; —$R^3N(R^4)C(N)R^4$; and —$R^3C(O)N(R^4)_2$; wherein the chain with its substituents, if any, must be charged;
  - (e) $R^6$—L—; wherein $R^6$—L— with its substituents, if any, must be charged; where
    - (i) L is selected from the group consisting of covalent bond; N; —N($R^5$)$_2^+$; S; O; a saturated or unsaturated $C_1$–$C_{15}$ alkyl chain, where said alkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and a saturated or unsaturated heteroalkyl chain having from 2 to 15 chain atoms, where one or more of said chain atoms is N, S, or O, and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and
    - (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings and unsaturated monocyclic or polycyclic heterocyclic rings wherein $R^6$ is unsubstituted or is substituted with one or more substituents independently selected from the group consisting of hydrogen; —$R^3$ $SR^1$; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —$R^3OR^4$; —$R^3CO_2R^4$; —$R^3O_2CR^4$; —$R^3N(R^4)_2$; $R^3$[—

$N(R^5)_3]+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; unsubstituted aryl or aryl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and hydroxy; and (3)
(a) $R^1$ is independently selected from the group consisting of hydrogen; —$C(O)R^7$; $C(S)R^7$; —$C(O)N(R^7)_2$; —$C(O)OR^7$; —$C(S)N(R,7)_2$; and —$C(S)OR^7$; where $R^7$ is hydrogen or unsubstituted $C_1$–$C_8$ alkyl or $C_1$–$C_8$ alkyl substituted win one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylallcyl, or alkynyl;

(b) $R^2$ is unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(c) $R^3$ is selected from the group consisting of covalent bond and unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) $R^4$ is independently selected from the group consisting of hydrogen; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and —$R^2SR^1$; and (e) $R^5$ is independently selected from the group consisting of unsubstituted $C_1$–$C_{15}$ alkyl or $C_1$–$C_{15}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; unsubstituted phenyl or phenyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; benzyl; and —$R^2SR^1$.

2. A compound according to claim 1, wherein A is hydroxy; and wherein B is a saturated or unsaturated heteroalkyl chain having from 2 to 15 chain atoms, where one or more of said chain atoms is nitrogen, and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; or B is $R^6$—L—.

3. A compound according to claim 1 wherein B is $R^6$—L—.

4. A compound according to claim 3, wherein L is covalent bond, $N,N(R^5)_2^\pm$, a $C_1$–$C_{15}$ alkyl chain, or a nitrogen containing heteroalkyl chain having from 2 to 15 chain atoms.

5. A compound according to claim 4, wherein L is a $C_1$–$C_{15}$ alkyl chain.

6. A compound according to claim 5, wherein said $C_1$–$C_{15}$ alkyl chain is substituted with one or more substituents selected from the group consisting of —$R^3SR^1$; hydrogen; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —$R^3OR^4$; and —$R^3CO_2R^4$.

7. A compound according to claim 4, wherein L is a nitrogen containing heteroalkyl chain having from 2 to 15 chain atoms.

8. A compound according to claim 7, wherein said nitrogen containing heteroalkyl chain is substituted with one or more substituents selected from the group consisting of —$R^3SR^1$; hydrogen; —$R^3N(R^4)_2$; —$R^3[N(R^5)_3]+$; and —$R^3N(R^4)C(O)R^4$.

9. A compound according to claim 3, wherein $R^6$ is a monocyclic heterocyclic moiety.

10. A compound according to claim 9, wherein $R^6$ is a six-membered heterocyclic ring moiety selected from the group consisting of pyridine, pyrridine, piperidine, pyridinium, pyrimidinium, and piperidinium; or $R^6$ is a five-membered heterocyclic ring moiety selected from the group consisting of imidazol, pyrrole, pyrrolidine, imidazolium, pyrrolium, and pyrrolidinium.

11. A compound according to claim 3, wherein $R^6$ is a polycyclic heterocyclic moiety.

12. A compound according to claim 11, wherein $R^6$ is a six-membered ring fused to a five-membered ring, said polycyclic heterocycle being selected from the group consisting of indol, indolium, pyrindine, imidazol-(1,2-a-)pyridine, imidazol-(1,2-a-)pyridinium, and pyrindinium; or $R^6$ is a six-membered ring fused to a six-membered ring, said polycyclic heterocycle being selected from the group consisting of quinoline, isoquinoline, tetrahydroquinoline, octahyrdroquinoline, quinolinium, isoquinolinium, tetrahydroquinolinium, or octahydroquinolinium.

13. A compound according to claim 3, wherein $R^6$ is a monocyclic carbocyclic moiety.

14. A compound according to claim 13, wherein $R^6$ is cycloheptyl or cyclohexyl.

15. A compound according to claim 3, wherein $R^6$ is substituted with one or more substituents selected from the group consisting of hydrogen; —$R^3SR^1$; —$R^3N(R^4)_2$; $R^3[-N(R^5)_3]+$; and —$R^3N(R^4)C(O)R^4$.

16. A compound according to claim 2, wherein B is a heteroalkyl chain having from 2 to 15 chain atoms where one or more chain atoms is nitrogen.

17. A compound according to claim 16, wherein said heteroalkyl chain is substituted with one or more substituents selected from the group consisting of —R$^3$SR$^1$; hydrogen; unsubstituted C$_1$–C$_8$ alkyl or C$_1$–C$_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —R$^3$OR$^4$; —R$^3$CO$_2$R$^4$; —R$^3$N(R$^4$)$_2$; —R$^3$[N(R$^5$)$_3$]+; and —R$^3$N(R$^4$)C(O)R$^4$.

18. A compound according to claim 2, wherein R$^4$ is hydrogen.

19. A compound according to claim 2, wherein R$^1$ is hydrogen; —C(O)R$^7$; C(S)R$^7$; or C(O)N(R$^7$)$_2$.

20. A compound according to claim 1, wherein A and B, together with C*, form a bicyclic ring, where both and X and X' are carbon atoms.

21. A compound according to claim 20, wherein W is a five-membered carbocyclic ring comprising C*, X, and X'.

22. A compound according to claim 21, wherein V is a five-membered ring or a six-membered ring.

23. A compound according to claim 22, wherein V is a heterocycle containing at least one ring nitrogen atom.

24. A compound according to claim 20, wherein said bicyclic ring is substituted with one or more substituents selected from the group consisting of —R$^3$SR$^1$; hydrogen; unsubstituted C$_1$–C$_8$ alkyl or C$_1$–C$_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —R$^3$OR$^4$; —R$^3$CO$_2$R$^4$; —R$^3$O$_2$CR$^4$; —R$^3$N(R$^4$)$_2$; —R$^3$[N(R$^5$)$_3$]+; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$.

25. A compound according to claim 24, wherein said bicyclic ring is substituted with one or more of —R$^3$SR$^1$; hydrogen; —R$^3$N(R$^4$)$_2$; —R$^3$CO$_2$R$^4$; —R$^3$[N(R$^5$)$_3$]+; or —R$^3$N(R$^4$)C(O)R$^4$; and R$^4$ is R$^3$SR$^1$ or hydrogen.

26. A compound according to claim 25, wherein R$^1$ is hydrogen; —C(O)R$^7$; —C(S)R$^7$; or —C(O)N(R$^7$)$_2$.

27. A phosphonosulfonate, or the pharmaceutically-acceptable salt or ester thereof, according to formula (I)

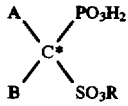

(I)

wherein (A)

(1) A is hydroxy; and (2) B is

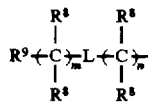

wherein (a) m is an integer from 0 to 10; n is an integer from 0 to 10; and m+n is an integer from 0 to 10;

(b) R$^8$ is independently selected from the group consisting of covalent bond; R$^3$ SR$^1$; hydrogen; unsubstituted C$_1$–C$_8$ alkyl or C$_1$–C$_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —R$^3$OR$^4$; —R$^3$CO$_2$R$^4$; —R$^3$O$_2$CR$^4$; —R$^3$N(R$^4$)$_2$; —R$^3$[N(R$^5$)$_3$]+; —R$^3$N(R$^4$)C(O)R$^4$—R$^3$N(R$^4$)C(S)R$^4$; —R$^3$N(R$^4$)C(N)R$^4$; —R$^3$C(O)N(R$^4$)$_2$; halogen; —R$^3$C(O)R$^4$; nitro; hydroxy; a saturated monocyclic or polycyclic carbocyclic ring, wherein said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl or alkynyl; an unsaturated monocyclic or polycyclic carbocyclic ring, wherein said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, arloxy, arylalkyl, or alkynyl; a saturated monocyclic or polycyclic heterocyclic ring, where said heterocyclic ring is unsubstituted or is substituted with one or more of alkyl, alkenyl, alkoxy, hydroxy, oxo, thioxo, amino, aminoalkyl, cyano, quaternary amino, quaternary. aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and an unsaturated monocyclic or polycyclic heterocyclic ring, where said heterocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(c) R$^1$ is independently selected from the group consisting of hydrogen; —C(O)R$^7$; —C(S)R$^7$; —C(O)N(R$^7$)$_2$; —C(O)OR$^7$; —C(S)N(R$^7$)$_2$; and —C(S)OR$^7$; where R$^7$ is hydrogen or unsubstituted C$_1$–C$_8$ alkyl or C$_1$–C$_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) R$^3$ is selected from the group consisting of covalent bond and unsubstituted C$_1$–C$_8$ alkyl or C$_1$–C$_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(e) R⁴ is independently selected from the group consisting of hydrogen; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and —R²SR¹;

(f) R⁵ is independently selected from the group consisting of unsubstituted $C_1$–$C_{35}$ alkyl or $C_1$–$C_{35}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; unsubstituted phenyl or phenyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; benzyl; and —R²SR¹;

(g) L is selected from the group consisting of covalent bond; —N(R⁸)—; [—N(R⁵)₂—]+; —S—; —O—; and —D—C(=E)—S—, where D is selected from the group consisting of covalent bond, O, or S, and E is O or S; and wherein (i) when L is —N(R⁸)—, or when L is [—N(R⁵)₂—]+ and m is an integer from 1 to 10, R⁹ is independently selected from the group consisting of covalent bond; hydrogen; unsubstituted $C_1$–$C_{35}$ alkyl or $C_1$–$C_{35}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; R²SR¹; and R¹⁰;

(ii) when L is [—N(R⁵)₂—]+ and m=0, R⁹ is selected from the group consisting of unsubstituted $C_1$–$C_{35}$ alkyl or $C_1$–$C_{35}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; R²SR¹; and R¹⁰; or (iii) when L is covalent bond, —S—, —O—, or —D—C(=E)—S, R⁹ is R¹⁰.

(h) R¹⁰ is a saturated, unsaturated, or aromatic monocyclic or polycyclic carbocycle or a saturated, unsaturated, or aromatic monocyclic or polycyclic heterocycle containing one or more heteroatoms; where said carbocycle or heterocycle is substituted with one or more R¹¹ substituents; and (i) each R¹¹ is independently selected from the group consisting of —R³SR¹; hydrogen; substituted or unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —R³OR⁴; —R³CO₂R⁴; —R³O₂CR⁴; —R³N(R⁴)₂; R³[—N(R⁵)3]+; —R³N(R⁴)C(O)R⁴; —R³N(R⁴)C(S)R⁴; —R³N(R⁴)C(N)R⁴; —R³C(O)N(R⁴)₂; halogen; —R³C(O)R⁴; hydroxy; unsubstituted arylalkyl or arylalkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; nitro; and unsubstituted aryl or aryl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

or (B) A and B are covalently linked together with C* to form a monocyclic or bicyclic ring having the following structure:

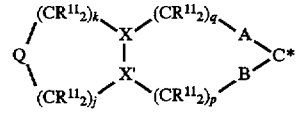

wherein (a) A and B are independently selected from the group consisting of covalent bond, —O—, —S—, and —NR¹⁰—;

(b) Q is selected from the group consisting of covalent bond; —NR¹²—; and [—N(R¹³)₂—]+;

(c) X and X' are independently selected from C(R¹²) or N;

(d) each R¹² is independently selected from the group consisting of —R³ SR¹; hydrogen; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloallcyl, heteroaryl, heterocycloalkyl, imino, hydroxylalkyl, aryloxy, arylalkyl, or alkynyl; —R³OR⁴; —R³CO₂R⁴; —R³O₂CR⁴; —R³N(R⁴)₂; R³[—N(R⁵)3]+; —R³N(R⁴)C(O)R⁴; —R³C(O)N(R⁴)₂; halogen; —R³C(O)R⁴; hydroxy; unsubstituted arylalkyl or arylalkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; nitro and unsubstituted aryl or aryl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and (e) each $R^{13}$ is selected from the group consisting of covalent bond unsubstituted $C_1$–$C_{35}$ alkyl or $C_1$–$C_{35}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl halo carboxy, alkoacetyl thio, thiol, aryl cycloalkyl, heteroaryl heterocloalkyl, imino, hydroxylalkyl aryloxy, arylalkyl, or alkynyl; unsubstituted phenyl or phenyl substituted with one or more of alkyl, alkenyl, alkoxy, hydroxy, oxo, thioxo, amino aminoalkyl, cyano, quaternary amino, quaternary aminoalkyl, amidino, amidinoalkyl, halo, carboxy, alkoacetyl, thio, thiol, aryl, cycloalkyl, heteroaryl, heterocycloalkyl, imino, hydroxylalkyl, aryloxy, arylalkyl, or alkenyl; benzyl; and $R^2SR^1$;

(f) when Q is other than covalent bond, k and j and k+j are integers from 0 to 5; when Q is covalent bond, k and j and k+j are integers from 0 to 6; and (g) p and q and p+q are independently integers from 0 to 3; except that if Q is covalent bond, then at least one of $R^{11}$ or $R^{12}$ is selected from the group consisting of —$R^3N(R^4)_2$; $R^3[—N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl.

28. A pharmaceutical composition comprising:
(a) a safe and effective amount of a phosphonosulfonate compound according to claim 1; and
(b) pharmaceutically-acceptable carriers.

29. A pharmaceutical composition comprising:
(a) a safe and effective amount of a phosphono sulfonate compound according to claim 2; and
(b) pharmaceutically-acceptable carriers.

30. A pharmaceutical composition comprising:
(a) a safe and effective amount of a phosphonosulfonate compound according to claim 20; and
(b) pharmaceutically-acceptable carriers.

31. A pharmaceutical composition comprising:
(a) a safe and effective amount of a phosphonosulfonate compound according to claim 27; and
(b) pharmaceutically-acceptable carriers.

32. A method for treating or preventing pathological conditions associated with abnormal calcium and phosphate metabolism in humans or other mammals in need of such treatment, comprising administering to a human or other mammal a safe and effective amount of a phosphonosulfonate compound of claim 1.

33. A method for treating or preventing pathological conditions associated with abnormal calcium and phosphate metabolism in humans or other mammals in need of such treatment, comprising administering to a human or other mammal a safe and effective amount of a phosphonosulfonate compound, or the pharmaceutically-acceptable salt or ester thereof, according to formula (I):

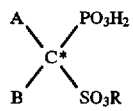

wherein
(A)
(1) A is selected from the group consisting of hydrogen; halogen; $SR^1$; $R^2SR^1$; amino; hydroxy; and unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(2) B is
(a) —$NH_2$;
(b) a saturated or unsaturated $C_1$–$C_{15}$ alkyl chain substituted with one or more substituents selected from the group consisting of —$R^3N(R^4)_2$; —$R^3[—N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$;

(c) a saturated or unsaturated heteroalkyl chain having from 2 to 15 chain atoms, where one or more of said chain atoms is nitrogen; and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) a saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[—N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$; or (e) $R^6$—L— where
(i) L is selected from the group consisting of covalent bond; N; —$N(R^5)_2^+$; S; O; a saturated or unsaturated $C_1$–$C_{15}$ alkyl chain, where said alkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and a saturated or unsaturated heteroalkyl chain having from 2 to 15 chain atoms, where one or more of said chain atoms is N, S, or O, and where said heteroalkyl chain is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and
(ii) $R^6$ is selected from the group consisting of saturated monocyclic or polycyclic carbocyclic rings; unsaturated monocyclic or polycyclic carbocyclic rings; saturated monocyclic or polycyclic heterocyclic rings and unsaturated monocyclic or polycyclic heterocyclic rings wherein $R^6$ is unsubstituted or is substituted with one or more substituents independently selected from the group consisting of hydrogen; —$R^3$ $SR^1$; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; —$R^3OR^4$; —$R^3CO_2R^4$; $R^3O_2CR^4$; —$R^3N(R^4)_2$; $R^3[\!\!-\!\!N(R^5)_3]+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; unsubstituted aryl or aryl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and hydroxy; and (3)
(a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or unsubstituted $C_1$–$C_8$ alkyl or $C_1$–$C_8$ alkyl substituted win one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(b) $R^2$ is unsubstituted C 1–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(c) $R^3$ is selected from the group consisting of covalent bond and unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

(d) $R^4$ is independently selected from the group consisting of hydrogen; unsubstituted $C_1$–$C_8$ alkyl or $C_1$–$C_8$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and —$R^2SR^1$; and (e) $R^5$ is independently selected from the group consisting of unsubstituted $C_1$–$C_{15}$ alkyl or $C_1$–$C_{15}$ alkyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; unsubstituted phenyl or phenyl substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; benzyl; and —$R^2SR^1$;

or (B) A and B are covalently linked together with C* to form a monocyclic ring of formula (a); or a bicyclic ring of formula (b):

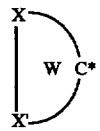

(a)

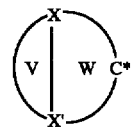

(b)

where
(1) W is a saturated or unsaturated carbocyclic ring formed by C*, X, and X', said carbocyclic ring having a total of from 3 to 6 ring carbon atoms, where said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; or a saturated or unsaturated heterocyclic ring formed by C*, X, and X', said heterocyclic ring having a total of from 4 to 6 ring atoms, where one or more of said ring atoms is N, O, or S, and where said heterocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heteroeycloalkyl, imino, hydroxylalkyl, aryloxy, arylalkyl, or alkynyl;

(2) V is a saturated or unsaturated carbocyclic ring formed by X and X', said carbocyclic ring having a total of from 3 to 8 ring carbon atoms, and where said carbocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl;

or a saturated or unsaturated heterocyclic ring formed by X and X', said heterocyclic ring having a total of from 3 to 8 ring atoms, where one or more of said ring atoms is N, O, or S, and where said heterocyclic ring is unsubstituted or is substituted with one or more of alkyl, alkenyl, alkoxy, hydroxy, oxo, thioxo, amino, aminoalkyl, cyano, quaternary amino, quaternary aminoalkyl, amidino, amidinoalkyl, halo, carboxy, alkoxyacetyl, thio, thiol, aryl, cycloalkyl, heteroaryl, heterocycloalkyl, imino, hydroxylalkyl, aryloxy, arylalkyl, or alkynyl; and (3) X and X' are independently N or C; except that if neither V nor W is a nitrogen containing heterocycle, then at least one of V or W is substituted with one or more substituents selected from the group consisting of —$R^3N(R^4)_2$; $R^3[-N(R^5)_3]+$; —$R^3N(R^4)C(O)R^4$; —$R^3N(R^4)C(S)R^4$; —$R^3N(R^4)C(N)R^4$; and —$R^3C(O)N(R^4)_2$;

and wherein R is selected from the group consisting of hydrogen, lower alkyl, lower acyloxyalkyl, aminocarbonyloxyalkyl, pivaloyloxymethyl, lactonyl, lower alkoxyacyloxyalkyl, alkoxyalkyl, choline and acylamino alkyl.

* * * * *